(12) United States Patent
Choi et al.

(10) Patent No.: US 12,344,647 B2
(45) Date of Patent: *Jul. 1, 2025

(54) FORMULATION OF MODIFIED INTERLEUKIN-7 FUSION PROTEIN

(71) Applicant: Genexine, Inc., Seongnam-si (KR)

(72) Inventors: Donghoon Choi, Seongnam-si (KR); Changyong Eun, Seoul (KR); Seong Hoon Jeong, Goyang-si (KR); Jun Yeul Lim, Busan (KR)

(73) Assignee: Genexine, Inc., Seongnam-si (KR)

( * ) Notice: Subject to any disclaimer, the term of this patent is extended or adjusted under 35 U.S.C. 154(b) by 192 days.

This patent is subject to a terminal disclaimer.

(21) Appl. No.: 18/053,671

(22) Filed: Nov. 8, 2022

(65) Prior Publication Data

US 2023/0279069 A1 Sep. 7, 2023

Related U.S. Application Data

(63) Continuation of application No. 15/773,273, filed as application No. PCT/KR2016/012495 on Nov. 2, 2016, now Pat. No. 11,548,927.

(30) Foreign Application Priority Data

Nov. 6, 2015 (KR) ........................ 10-2015-0156124

(51) Int. Cl.
| | | |
|---|---|---|
| C07K 14/54 | (2006.01) | |
| A61K 9/08 | (2006.01) | |
| A61K 38/20 | (2006.01) | |
| A61K 47/10 | (2017.01) | |
| A61K 47/12 | (2006.01) | |
| A61K 47/18 | (2017.01) | |
| A61K 47/26 | (2006.01) | |
| C07K 5/062 | (2006.01) | |
| C07K 5/083 | (2006.01) | |
| C07K 5/103 | (2006.01) | |
| C07K 7/06 | (2006.01) | |

(52) U.S. Cl.
CPC ............ *C07K 14/5418* (2013.01); *A61K 9/08* (2013.01); *A61K 38/2046* (2013.01); *A61K 47/10* (2013.01); *A61K 47/12* (2013.01); *A61K 47/183* (2013.01); *A61K 47/26* (2013.01); *C07K 7/06* (2013.01); *C07K 14/54* (2013.01); *C07K 5/06026* (2013.01); *C07K 5/0606* (2013.01); *C07K 5/0806* (2013.01); *C07K 5/081* (2013.01); *C07K 5/1008* (2013.01); *C07K 5/1013* (2013.01); *C07K 2319/30* (2013.01)

(58) Field of Classification Search
CPC ............ C07K 14/5418; C07K 2319/30; A61K 38/2046; A61K 9/08

See application file for complete search history.

(56) References Cited

U.S. PATENT DOCUMENTS

| | | | |
|---|---|---|---|
| 5,093,242 | A | 3/1992 | Bachmair et al. |
| 6,153,380 | A | 11/2000 | Nolan et al. |
| 7,585,947 | B2 | 9/2009 | Morre et al. |
| 7,589,179 | B2 | 9/2009 | Gillies et al. |
| 8,153,114 | B2 | 4/2012 | Morre et al. |
| 10,208,009 | B2 | 2/2019 | Rho et al. |
| 10,208,099 | B2 | 2/2019 | Yang et al. |
| 11,357,827 | B2 | 6/2022 | Kang et al. |
| 11,548,927 | B2 | 1/2023 | Choi et al. |
| 11,708,399 | B2 | 7/2023 | Kang et al. |
| 2002/0127564 | A1 | 9/2002 | Nolan |
| 2005/0054054 | A1* | 3/2005 | Foss ................... C07K 14/5418 435/325 |
| 2005/0164352 | A1* | 7/2005 | Lauder .................... A61P 37/02 435/328 |
| 2005/0249701 | A1 | 11/2005 | Morre et al. |
| 2006/0141581 | A1* | 6/2006 | Gillies .................... A61P 35/00 435/325 |
| 2008/0206190 | A1 | 8/2008 | Morre et al. |
| 2008/0300188 | A1* | 12/2008 | Yang ........................ A61P 7/00 435/325 |
| 2010/0196312 | A1 | 8/2010 | Morre et al. |

(Continued)

FOREIGN PATENT DOCUMENTS

| | | |
|---|---|---|
| CN | 105012949 A | 11/2015 |
| EP | 0314415 A2 | 5/1989 |

(Continued)

OTHER PUBLICATIONS

Bowie et al. Deciphering the Message in Protein Sequences: Tolerance to Amino Acid Substitutions. Science, 1990, 247:1306-1310 (Year: 1990).*

(Continued)

*Primary Examiner* — Vanessa L. Ford
*Assistant Examiner* — Sandra Carter
(74) *Attorney, Agent, or Firm* — Sterne, Kessler, Goldstein & Fox P.L.L.C.

(57) ABSTRACT

Provided is a pharmaceutical formulation comprising a modified IL-7 protein. More particularly, it comprises (a) a modified IL-7 fusion protein; (b) a basal buffer with a concentration of 10 to 50 mM; (c) a sugar with a concentration of 2.5 to 5 w/v %; and (d) a surfactant with a concentration of 0.05 to 6 w/v %.

Such pharmaceutical formulation of a modified IL-7 fusion protein does not show aggregates formation, but shows protective effects on proteins under stress conditions such as oxidation or agitation, and thus can effectively be used for the treatment of a patient.

20 Claims, 13 Drawing Sheets

Specification includes a Sequence Listing.

(56) References Cited

U.S. PATENT DOCUMENTS

| | | |
|---|---|---|
| 2011/0243887 A1 | 10/2011 | Lauder et al. |
| 2012/0016104 A1 | 1/2012 | Morre et al. |
| 2013/0217864 A1 | 8/2013 | Cho et al. |
| 2014/0178393 A1 | 6/2014 | Andres et al. |
| 2014/0377218 A1 | 12/2014 | Morre et al. |
| 2015/0306224 A1 | 10/2015 | Krause et al. |

FOREIGN PATENT DOCUMENTS

| | | | |
|---|---|---|---|
| EP | 0877752 B1 | 5/2003 | |
| JP | H02501618 A | 6/1990 | |
| JP | 250198618 B2 | 5/1996 | |
| JP | 2000504220 A | 4/2000 | |
| JP | 2001509661 A | 7/2001 | |
| JP | 2009501543 A | 1/2009 | |
| JP | 2010531134 A | 9/2010 | |
| JP | 2014147396 A | 8/2014 | |
| JP | 201557392 A | 3/2015 | |
| KR | 1020060112673 A | 11/2006 | |
| KR | 1020090045953 A | 5/2009 | |
| KR | 1020120041139 A | 4/2012 | |
| KR | 1020140004802 A1 | 1/2014 | |
| KR | 1020170066265 A | 6/2017 | |
| WO | WO-8802406 A | 4/1988 | |
| WO | WO-2005021592 A2 | 3/2005 | |
| WO | WO-2009101737 A1 | 6/2011 | |
| WO | WO-2015015516 A2 | 2/2015 | |
| WO | WO-2007019232 A2 * | 2/2017 | ........... A61K 39/395 |
| WO | WO-2017078385 A1 | 5/2017 | |

OTHER PUBLICATIONS

Burgess et al. Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue. J. Cell Biol. 111:2129-2138, 1990 (Year: 1990).*

Lazar et al. Transforming Growth Factor alpha: Mutation of Aspartic Acid 47 and Leucine 48 Results in Different Biological Activities. Mol. Cell. Biol., 8:1247-1252, 1988 (Year: 1988).*

Bork. Powers and Pitfalls in Sequence Analysis: The 70% Hurdle. Genome Research, 2000; 10:398-400 (Year: 2000).*

Greenspan et al. 1999. Defining epitopes: It's not as easy as it seems; Nature Biotechnology, 17:936-937 (Year: 1999).*

NCBI, PDB: 4C54_A (Feb. 5, 2014), "Chain A, Crystal Structure of Recombinant Human IgG4 Fc".

International Search Report for International Application No. PCT/KR2016/012495, Korean Intellectual Property Office, Republic of Korea, mailed on Jan. 13, 2017, 4 pages.

Fry, T., and Mackall C.L, "Interleukin-7: from bench to clinic," Blood 99(11):3892-3904, American Society of Hematology, United States (Jun. 2002).

GenBank, "Interleukin-7 [synthetic construct]," Accession No. AAB70834.1, accessed at https://www.ncbi.nlm.nih.gov/protein/AAB70834.1/, accessed on Apr. 28, 2023, 1 page.

Heufler, C., et al., "Interleukin 7 is produced by murine and human keratinocytes," J Exp Med 178(3):1109-1114, Rockefeller University Press, United States (Sep. 1993).

International Preliminary Report on Patentability and Written Opinion of the International Searching Authority issued Dec. 12, 2017 for related PCT/KR2016/006214.

International Search Report for International Application No. PCT/KR2016/006214, Korean Intellectual Property Office, Republic of Korea, mailed on Aug. 24, 2016, 6 pages.

Kroncke, R., et al., "Human follicular dendritic cells and vascular cells produce interleukin-7: a potential role for interleukin-7 in the germinal center reaction," Eur J Immunol 26(10):2541-2544, Wiley-VCH, Germany (Oct. 1996).

Pellegrini, M., et al., "IL-7 engages multiple mechanisms to overcome chronic viral infection and limit organ pathology," Cell 144(4):601-613, Cell Press, United States (Feb. 2011).

Muegge, K., et al., "Interleukin-7: a cofactor for V(D)J rearrangement of the T cell receptor beta gene," Science 261(5117):93-95, American Association for the Advancement of Science, United States (Jul. 1993).

Nanjappa, S., et al., "Immunotherapeutic effects of IL-7 during a chronic viral infection in mice," Blood 117(19):5123-5132, American Society of Hematology, United States (May 2011).

Patel, A., et al., "Treatment of progressive multifocal leukoencephalopathy and idiopathic CD4+ lymphocytopenia," J Antimicrob Chemother 65(12):2489-2492, Oxford University Press, United Kingdom (Dec. 2010).

Pellegrini, M., et al., "Adjuvant IL-7 antagonizes multiple cellular and molecular inhibitory networks to enhance immunotherapies," Nat Med 15(5):528-536, Nature Portfolio, Germany (May 2009).

Rosenberg, S., et al., "IL-7 administration to humans leads to expansion of CD8+ and CD4+ cells but a relative decrease of CD4+ T-regulatory cells," J Immunother 29(3):313-319, Lippincott Williams & Wilkins, United States (May-Jun. 2006).

Sawa, Y., et al., "Hepatic interleukin-7 expression regulates T cell responses," Immunity 30(3):447-457, Cell Press, United States (Mar. 2009).

Snyder, K.M., et al., "IL-7 in allogeneic transplant: clinical promise and potential pitfalls," Leuk Lymphoma 47(7):1222-1228, Informa, United Kingdom (Jul. 2006).

Watanabe, M., et al., "Interleukin 7 is produced by human intestinal epithelial cells and regulates the proliferation of intestinal mucosal lymphocytes," J Clin Invest 95(6):2945-2953, American Society for Clinical Investigation, United States (Jun. 1995).

European Patent Office; Search Report dated Dec. 19, 2018 issued in Counterpart U.S. Appl. No. 16/807,859.

Japanese Patent Office; Search Report dated Jan. 8, 2019 issued in Counterpart Application No. 2017-564121.

European Patent Office; Communication dated May 15, 2019 in Counterpart Application No. 16807859.0.

Mikayama, T., et al., "Molecular cloning and functional expression of a cDNA encoding glycosylation-inhibiting factor," Proc Natl Acad Sci USA 90(21):10056-10060, National Academy of Sciences, United States (Nov. 1993).

Voet et al., Biochemistry John Wiley & Sons Inc. (1990) pp. 126-128 and 228-234.

International Search Report for International Application No. PCT/KR2016/013966, Korean Intellectual Property Office, Republic of Korea, mailed on Mar. 2, 2017, 4 pages.

Moon Cheol Kang, et al., "Intranasal Introduction of Fc-Fused Interleukin-7 Provides Long-Lasting Prophylaxis against Lethal Influenza Virus Infection," J Virol 90(5):2273-2284, American Society of Microbiology, United States (Dec. 2015).

Nam, H.J., et al., "Marked enhancement of antigen-specific T-cell responses by IL-7-fused nonlytic, but not lytic, Fc as a genetic adjuvant," Eur J Immunol 40(2):351-358, Wiley-VCH, Germany (Feb. 2010).

Yong Bok Seo, et al., "Crucial roles of interleukin-7 in the development of T follicular helper cells and in the induction of humoral immunity," J Virol 88(16):8998-9009, American Society of Microbiology, United States (Aug. 2014).

Bowie, J., et al., "Deciphering the message in protein sequences: tolerance to amino acid substitutions," Science 247(4948):1306-1310, American Association for the Advancement of Science, United States (Mar. 1990).

Burgess, W.H., et al., "Possible dissociation of the heparin-binding and mitogenic activities of heparin-binding (acidic fibroblast) growth factor-1 from its receptor-binding activities by site-directed mutagenesis of a single lysine residue," J Cell Biol 111(5 Pt 1):21219-2138, Rockefeller University Press, United States (Nov. 1990).

Lazar, E., et al., "Transforming growth factor alpha: mutation of aspartic acid 47 and leucine 48 results in different biological activities," Mol Cell Biol 8(3):1247-1252, American Society for Microbiology, United States (Mar. 1988).

Bork, P., "Powers and pitfalls in sequence analysis: the 70% hurdle," Genome Res 10(4):398-400, Cold Spring Harbor Laboratory Press, United States (Apr. 2000).

(56) References Cited

OTHER PUBLICATIONS

International Search Report for International Application No. PCT/KR2016/014127, Korean Intellectual Property Office, Republic of Korea, mailed on Mar. 9, 2017, 4 pages.
Whisstock, J., and Lesk, A., "Prediction of protein function from protein sequence and structure," Q Rev Biophys 36(3):307-340, Cambridge University Press, United Kingdom (Aug. 2003).
Maryam Fazeli et al., "Efficacy of HPV-16 E7 Based Vaccine in a TC-1 Tumoric Animal Model of Cervical Cancer," Cell Journal 12(4):483-488, Cell Press, United States (2011).
Greenspan, N.S., et al., "Defining epitopes: It's not as easy as it seems," Nature Biotechnology, 17:936-937, Springer, Germany (Oct. 1999).
Buchman, A., et al., "Comparison of Intron-Dependent and Intron-Independent Gene Expression," Molecular and Cellular Biology 8(10):4395-4405, American Society for Microbiology, United States (Oct. 1988).

\* cited by examiner

FORMULATION OF MODIFIED INTERLEUKIN-7 FUSION PROTEIN

CROSS REFERENCE TO RELATED APPLICATIONS

This application is continuation application of U.S. patent application Ser. No. 15/773,273 (currently allowed), which is a U.S. National Stage of International Application No. PCT/KR2016/012495, filed on Nov. 2, 2016, which claims the priority benefit of Korean Patent Application No. 10-2015-0156124, filed on Nov. 6, 2015, each of which is hereby incorporated by reference in its entirety.

REFERENCE TO SEQUENCE LISTING SUBMITTED ELECTRONICALLY VIA EFS-WEB

The content of the electronically submitted sequence listing in ASCII text file (Name: 4241_0330002_Seglisting_ST26.xml; Size: 62,076 bytes; and Date of Creation: Oct. 31, 2022) filed with the application is incorporated herein by reference in its entirety.

TECHNICAL FIELD

The present invention relates to a formulation of a pharmaceutical composition comprising a modified interleukin-7 fusion protein.

BACKGROUND ART

Interleukin-7 (IL-7) is a cytokine stimulating immune responses mediated by T cell and B cell, and specifically, it plays an important role in an adaptive immune system. Although IL-7 is mainly secreted by stromal cells in the bone marrow and the thymus, it is also produced in keratinocytes, dendritic cells, hepatocytes, neural and epithelial cells (Heufler C et al., 1993, *J. Exp. Med.* 178 (3): 1109-14; Kroncke R et al., 1996, *Eur. J. Immunol.* 26 (10): 2541-4: Sawa Y et al., 2009, *Immunity* 30 (3): 447-57; Watanabe M et al., 1995, *J. Clin. Invest.* 95 (6): 2945-53).

IL-7 actives the immune system by influencing the survival and differentiation of T cell and B cell, and stimulating the activity of NK (natural killer) cell, and so on, and specifically, it plays an important role in the development of B cell. IL-7 enhances the immune response in the human body by stimulating the secretion of IL-2, a type of cytokine, and interferon-γ.

In other words, IL-7 is a cytokine which promotes the survival and proliferation of T-cell, B-cell and other immune cells, and is an excellent candidate for an immune therapeutic agent applicable to various disorders such as viral infection, cancer and immune system damage. Recently a clinical study has been conducted to elucidate the effect by IL-7 on various malignancies and human immune deficiency virus infection, and as a result, an immune enhancing effect in human of IL-7 was reported (Fry T J et al., 2002, *Blood* 99 (11): 3892-904; Muegge K et al., 1993, *Science* 261 (5117): 93-5; Rosenberg S A et al., *J. Immunother.* 29 (3): 313-9). In addition, IL-7 has been reported to be helpful in the immune recovery after allogenic stem cell transplantation (Snyder K M, 2006, *Leuk Lymphoma* 47 (7). 1222-8), and is used for the treatment of lymphopenia as well. Accordingly, IL-7 reorganizes immune cells, enhances T cell function, and competes with the substances which induce immunosuppression, and thus it can be used for treating cancer or chronic infection.

However, in order to utilize proteins such as IL-7 for a pharmaceutical use, it is necessary to prepare a suitable formulation in consideration of the structure and the physiochemical stability in surrounding environment of the protein. In addition, the physical and chemical stability of the protein is affected by external factors such as manufacturing of a pharmaceutical formulation, purification of a protein, and storage. In general, a protein is structurally and thermodynamically unstable, and thus is easily subject to aggregates formation or physiochemical degradation. In addition, when Fc region of an immunoglobulin is used as a fusion partner, the physiochemical property of the entire fusion protein such as thermodynamic property, Zeta potential and stress stability, etc., can vary greatly since the Fc region has a large molecular weight and a complex structure. Specifically, little is known with respect to a stabilized formulation for the modified IL-7 fusion protein. Thus, it is necessary to optimize the formulation of a protein in order to increase the stability of the protein for a pharmaceutical use.

DISCLOSURE OF INVENTION

Technical Problem

Therefore, the present inventors have established an appropriate formulation to increase the stability of a modified IL-7 fusion protein for use in treating a variety of disorders.

An object of the present invention is to provide a pharmaceutical formulation comprising a modified IL-7 fusion protein with increased stability.

Solution to Problem

In accordance with the object of the present invention, there is provided a pharmaceutical formulation comprising: (a) a modified IL-7 fusion protein; (b) a basal buffer with a concentration of 10 to 50 mM; (c) a sugar with a concentration of 2.5 to 5 w/v %; and (d) a surfactant with a concentration of 0.05 to 6 w/v %.

Advantageous Effects of Invention

A pharmaceutical formulation of a modified IL-7 fusion protein according to the present invention does not show aggregates formation, and maintains stability of the modified IL-7 fusion protein under stress conditions such as oxidation or agitation, and thus can be used for the treatment of a patient.

MODE FOR THE PRESENT INVENTION

Figure 1:
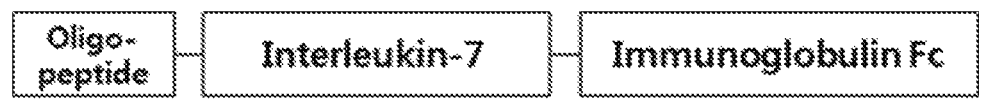
FIG. 1 is a schematic diagram showing the structure of a modified IL-7 fusion protein according to the present invention.

Hereinafter, the present invention will be described in detail.

The present invention provides a pharmaceutical formulation comprising (a) a modified IL-7 fusion protein; (b) a basal buffer with a concentration of 10 to 50 mM; (c) a sugar with a concentration of 2.5 to 5 w/v %; and (d) a surfactant with a concentration of 0.05 to 6 w/v %.

As used herein, the term "interleukin-7 (IL-7)" refers to a hematopoietic growth factor, which is expressed in or secreted by various stromal cells, keratin-producing cells, dendritic cells, neurons, epidermal cells, etc. IL-7 may promote an immune response by binding to a receptor, and activate a variety of immune cells such as T cell, B cell, mononuclear cell involved in the immune system.

Such IL-7 is either interleukin-7 (IL-7) or a polypeptide having a similar activity to IL-7.

IL-7 the present invention includes the polypeptides consisting of the amino acid sequences represented by SEQ ID NOs:1 to 6. In addition, the amino acid sequence of the IL-7 fusion protein may have a sequence homology of about 90%, 91%, 92%, 93%, 94%, 95%, 96%, 97%, 98%, 99% or more to the sequences of SEQ ID NOs: 1 to 6. IL-7 may be an IL-7 fusion protein or a fusion protein comprising a fragment thereof. In addition, IL-7 may be derived from human, rat, mouse, monkey, cow or sheep.

Specifically, human-derived IL-7 may have the amino acid sequence represented by SEQ ID NO:1 (Genbank Accession No. P13232); rat-derived IL-7 may have the amino acid sequence represented by SEQ ID NO:2 (Genbank Accession No. P56478); mouse-derived IL-7 may have the amino acid sequence represented by SEQ ID NO:3 (Genbank Accession No. P10168); monkey-derived IL-7 may have the amino acid sequence represented by SEQ ID NO:4 (Genbank Accession No. NP_001279008); bovine IL-7 may have the amino acid sequence represented by SEQ ID NO:5 (Genbank Accession No. P26895); and sheep-derived IL-7 may have the amino acid sequence represented by SEQ ID NO:6 (Genbank Accession No. Q28540).

As used herein, the term "modified IL-7" refers to a molecule wherein an oligopeptide composed of 1 to 10 amino acids is present at the terminal of IL-7, thereby to have a different sequence from the wild type IL-7.

Preferably, a modified IL-7 according to the present invention has the following structure:

A–IL-7;
wherein said A may be bound to the N-terminal of the IL-7. The nucleic acid encoding said A may be present with IL-7 genes sequentially on a DNA construct, which may be expressed as a protein. Further, said A may be expressed or synthesized independently, and then bound to IL-7 by a chemical bond.

Said A may comprise 1 to 10, specifically 2 to 8, more specifically 1 to 5 amino acids, wherein the comprised amino acid may be selected from the group consisting of methionine (M), glycine (G), and a combination thereof. Examples of said A include M, G, MM, MG, GM, GG, MMM, GMM, MGM, MMG, GGM, GMG, MGG, GGG, MMMM (SEQ ID NO:9), GMMM (SEQ ID NO:10), MGMM (SEQ ID NO:11), MMGM (SEQ ID NO:12), MMMG (SEQ ID NO:13), GGMM (SEQ ID NO:14), MGGM (SEQ ID NO:15), MMGG (SEQ ID NO:16), GMGM (SEQ ID NO:17), MGMG (SEQ ID NO:18), GMMG (SEQ ID NO:19), GGGM (SEQ ID NO:20), MGGG (SEQ ID NO:21), GMGG (SEQ ID NO:22), GGMG (SEQ ID NO:23), GGGG (SEQ ID NO:24), MMMMM (SEQ ID NO:25), GMMMM (SEQ ID NO:26), GGMMM (SEQ ID NO:27), GGGMM (SEQ ID NO:28), GGGGM (SEQ ID NO:29), MGMMM (SEQ ID NO:30), MGGMM (SEQ ID NO:31), MGGGM (SEQ ID NO:32), MGGGG (SEQ ID NO:33), MMGMM (SEQ ID NO:34), MMGGM (SEQ ID NO:35), MMGGG (SEQ ID NO:36), MMMGM (SEQ ID NO:37), MMMGG (SEQ ID NO:38), MMMMG (SEQ ID NO:39), MGGGM (SEQ ID NO:40), MGMGM (SEQ ID NO:41), GMGMG (SEQ ID NO:42), GMMMG (SEQ ID NO:43), GGMGM (SEQ ID NO:44), GGMMG (SEQ ID NO:45), MGGMG (SEQ ID NO:46), MGMGG (SEQ ID NO:47), GMMGM (SEQ ID NO:48), MGMMG (SEQ ID NO:49), GMGGM (SEQ ID NO:50), MMGMG (SEQ ID NO:51), GMMGG (SEQ ID NO:52), GMGGG (SEQ ID NO:53), GGMGG (SEQ ID NO:54), GGGMG (SEQ ID NO:55) and GGGGG (SEQ ID NO:56), etc. According to an example of the present invention, said A may be M, MM, GM, MGM or MMM.

A modified IL-7 fusion protein according to the present invention may further comprise the Fc region of a modified immunoglobulin at the C-terminal thereof.

As used herein, the term "modified IL-7 fusion protein" refers to a molecule wherein a modified immunoglobulin Fc region is bound to the C-terminal of a modified IL-7.

Said modified immunoglobulin Fc region may be one whose binding activity to a Fc receptor or to a complement is modified, resulting in weakened antibody-dependent cellular cytotoxicity (ADCC) or complement dependent cytotoxicity (CDC). Such modification may be achieved by genetic mutation (i.e., substitution, deletion of the sequence) of the binding site for Fc gamma receptor (FcrR), Clq, and Fc binding receptor (FcRn) in the Fc region.

In addition, such modification may be achieved by mixing different types of immunoglobulin sequences, that is, by preparing a hybrid Fc.

As used herein, the term "Fc region", "Fc fragment" or "Fc" may include a hinge region, a heavy chain constant region 2 (CH2) domain, and a heavy chain constant region 3 (CH3) domain in the direction from the N-terminal to the C-terminal. Such region may further comprise a hinge region, in which case the hinge region may serve is as a linker, and may appropriately be modified to improve the property of the molecule.

The Fc region or a fragment thereof referred to as "hFc" or "hyFc" is a type of hybrid Fc, which is prepared by combining different types of Fc regions. Such hyFc may include a portion of a human IgD hinge region, an amino acid residue of a human IgD CH2 domain, an amino acid residue of a human IgG4 CH2 domain, and an amino acid residue of a human IgG4 CH3 domain.

The Fc region variant may be modified so as to prevent truncation at the hinge region. Specifically, the amino acid at position 144 and/or the amino acid at position 145 of SEQ ID NO: 7 can be modified. Preferably, K, the amino acid at position 144 of SEQ ID NO:7, may be substituted with G or S, and E, the amino acid at position 145 of SEQ ID NO:7, may be substituted with G or S, to form a variant.

In addition, two fusion proteins may form one dimer. For example, when the third domain is Fc region, the Fc regions may bind to each other to form a dimer.

According to an example of the present invention, the modified immunoglobulin Fc region may be a polypeptide consisting of the amino acid sequence represented by SEQ ID NO:7. The Fc region of a modified immunoglobulin according to the present invention may be one described in U.S. Pat. No. 7,867,491, and can be producted with reference to the description in U.S. Pat. No. 7,867,491.

According to an example of the present invention, the modified IL-7 may have the amino acid sequence of SEQ ID NO:8. In addition, the modified IL-7 may have a sequence homology of 90%, 91%, 92%, 93%, 94%, 95%, 96%, 97%, 98%, or 99% to the amino acid sequence of SEQ ID NO:8.

As used herein, the term "basal buffer" refers to a solution which endures a pH change by the action of an acid-base conjugate component contained therein.

A basal buffer according to the present invention may be histidine-acetate or sodium citrate solution. The basal buffer may be used in a concentration of 10 to 50 mM, 15 to 40 mM, or 20 to 30 mM. According to an example of the present invention, it may be used in a concentration of 20 mM.

The histidine-acetate solution is a buffer containing histidine ions. The histidine-acetate solution is prepared by titrating L-histidine with liquid acetic acid. Meanwhile, the sodium citrate solution is prepared by titrating the sodium citrate solution with hydrous citric acid regarding the final concentration and pH of the solution.

A sugar stabilizes the fusion protein in the present invention. In addition, a sugar is widely used as an excipient for pharmaceutical formulations as it is easily dissolved in water and has a sweet taste.

In a formulation according to the present invention, the sugar may be comprised in a concentration of 2.5 to 5 w/v %, 3.5 to 5 w/v %, or 4.5 to 5 w/v %, and particularly 5 w/v % in an example of the present invention.

In a formulation according to the present invention, the sugar may be sucrose, trehalose, dextrose, or a mixture thereof. In one example of the present invention, the sugar may be sucrose. Sucrose is a disaccharide formed of glucose and fructose by 1, 2-binding, which is relatively stable in an alkaline environment but may be easily hydrolyzed by an acid.

In a pharmaceutical formulation according to the present invention, a sugar has the effect of protecting a fusion protein from the oxidation stress, and a sugar alcohol may be used as a sugar substitute or an auxiliary substance. The sugar alcohol may be sorbitol, xylitol, maltitol, mannitol or a mixture thereof. In one example of the present invention, the sugar alcohol may be sorbitol.

As used herein, the term "surfactant" is a surface activating agent, and specifically, it refers to a non-ionic surfactant. In the pharmaceutical formulation according to the present invention, the surfactant inhibits aggregates formation of a fusion protein, thereby increasing the stability of the fusion protein.

In the formulation according to the present invention, a surfactant may be added in a concentration of 0.05 to 6 w/v %, 0.1 to 5.5 w/v %, or 0.1 to 5.0 w/v %.

The surfactant may be polysorbate, polyoxyethylene alkyl ether, polyoxyethylene stearate, alkyl sulfate, polyvinyl pyridone, poloxamer or a mixture thereof. Specifically, the surfactant may be polysorbate or poloxamer.

The polysorbate according to the present invention is a polyoxyethylene higher aliphatic alcohol formed by combinding sorbitan fatty acid ester with ethylene oxide, which may be polysorbate 20 (monolaurate), 40 (monopalmitate), 60 (monostearate), 65 (tristearate), or 80 (mono-oleate) based on the number of the polyoxyethylene group and the kind of the fatty acid. In addition, poloxamer is a polyoxy-propylene-polyoxyethylene block copolymer, which may vary depending on the length of the polymer.

In one example of the present invention, the surfactant may be polysorbate 20, polysorbate 80 or poloxamer 188.

A pharmaceutical formulation according to the present invention may further comprise an amino acid such as arginine, glutamate, glycine, histidine or a mixture thereof, etc. The amino acid is comprised as an excipient in order to stabilize a protein, and various amino acids may be comprised depending on the type of the protein. The amino acid may be arginine, glutamate, glycine or histidine, and according to an example of the present invention, it may be glutamate. The amino acid may be added in a concentration of 40 to 60 mM, according to an example of the present invention, 50 mM.

When using a pharmaceutical formulation of the present invention as an injection, it may further comprise a sugar alcohol to adjust the osmotic pressure. The sugar alcohol refers to a long-chain alcohol in which a carbonyl group of a sugar is reduced to a hydroxyl group (—OH). The sugar alcohol may be added such that the concentration thereof reaches 1 to 2 w/v %, and according to an example of the present invention, 1.5 w/v %.

Examples of sugar alcohol for use in the present invention include sorbitol, xylitol, maltitol, mannitol or a mixture thereof. According to an example of the present invention, the sugar alcohol may be sorbitol. Sorbitol is a sugar alcohol having 6 hydroxyl groups formed by high pressure addition and reduction of glucose, which is also referred to as D-sorbitol or D-glucitol.

The pharmaceutical formulation of the present invention may have a pH of 5.0 to 6.0, specifically 5.0. The conformational stability of a fusion protein decreases if the pH of the basal buffer is lower than 5.0, while the fusion protein may show aggregates formation depending on a specific composition if the pH exceeds 6.0.

The formulation may be a liquid formulation.

The inventors have prepared a modified IL-7 fusion protein in which an oligopeptide is bound to the N-terminal of IL-7 and the Fc region of an immunoglobulin is bound to the C-terminal of IL-7, and selected a basal buffer and an excipient to prepare a pharmaceutical formulation of the fusion protein First, stability of the modified IL-7 fusion protein depending on a basal buffer was examined at various pH conditions. When sodium citrate was used as a basal buffer, stability of the fusion protein increased as the pH increased (Table 2 and FIG. 2), but the zeta potential decreased and aggregates of the fusion protein were formed as the pH increased. When histidine-acetate was used as a basal buffer, similar results were obtained, and thus, the experiment was conducted at the condition of pH 5.0 first (Table 3 and FIG. 3).

In addition, to examine the protective effect on the fusion protein against the stress environments such as agitation and oxidation, a sugar or a sugar alcohol, a surfactant, and an amino acid were added as excipients. As a result, sucrose and sorbitol showed protective effect on the fusion protein against oxidation stress, while surfactants such as tween 20, Tween 80 and poloxamer 188 showed protective effect on the fusion protein against agitation stress, irrespective of the type of the surfactant. In the cases of further using an amino acid, the protective effect on the fusion protein according to the present invention was observed when arginine, glutamine, glycine, or histidine was added, among which glutamate showed an excellent protective effect (Table 4 and Table 5).

By the above method, Tween 80 and sucrose were selected, as showing a protective effect on the fusion protein, and the protective effect of the combination of the selected excipients was examined. As a result, a protective effect on the fusion protein against agitation or oxidation stress was shown when Tween 80 and sucrose were mixed in the histidine-acetate basal buffer. Also, the average change of about 1% was observed in a variety of stress conditions when sucrose, sorbitol, and Tween 80 were mixed in the histidine-acetate basal buffer, verifying that such formulation is excellent (Table 7, Table 8 and Table 10).

BEST MODE FOR CARRYING OUT THE PRESENT INVENTION

Hereinafter, the present invention is explained in detail by Examples. The following Examples are intended to further illustrate the present invention without limiting its scope.

Example 1: Preparation of Modified Interleukin-7 Fusion Proteins

Prepared was an IL-7 fusion protein in which an oligopeptide and an immunoglobulin Fc region were bound to the N-terminal and the C-terminal, respectively. The sequence of a human IL-7 (SEQ ID NO:1) was used for IL-7, and the combination sequence of methione (M) and glycine (G) was used for the oligopeptide. The Fc region is a hybrid of the Fc region of human IgD and the Fc region of human IgG4, which can increase in vivo half-life grately when binding to a bioactive fusion protein, compared to known modified Fc regions of immunoglobulins.

First, gene sequence which encodes the amino acid sequence of M-IL-7-hyFc, G-IL-7-hyFc, MM-IL-7-hyFc, MG-IL-7-hyFc, GM-IL-7-hyFc, GG-IL-7-hyFc, MMM-IL-7-hyFc, GMM-IL-7-hyFc, MGM-IL-7-hyFc, MMG-IL-7-hyFc, GGM-IL-7-hyFc, GMG-IL-7-hyFc, MGG-IL-7-hyFc, GGG-IL-7-hyFc, MMMM-IL-7-hyFc, GMMM-IL-7-hyFc, MGMM-IL-7-hyFc, MMGM-IL-7-hyFc, MMMG-IL-7-hyFc, GGMM-IL-7-hyFc, MGGM-IL-7-hyFc, MMGG-IL-7-hyFc, GMGM-IL-7-hyFc, MGMG-IL-7-hyFc, GMMG-IL-7-hyFc, GGGM-IL-7-hyFc, MGGG-IL-7-hyFc, GMGG-IL-7-hyFc, GGMG-IL-7-hyFc, GGGG-IL-7-hyFc, MMMMM-IL-7-hyFc, GMMMM-IL-7-hyFc, GGMMM-IL-7-hyFc, GGGMM-IL-7-hyFc, GGGGM-IL-7-hyFc, MGMMM-IL-7-hyFc, MGGMM-IL-7-hyFc, MGGGM-IL-7-hyFc, MGGGG-IL-7-hyFc, MMGMM-IL-7-hyFc, MMGGM-IL-7-hyFc, MMGGG-IL-7-hyFc, MMMGM-IL-7-hyFc, MMMGG-IL-7-hyFc, MMMMG-IL-7-hyFc, MGMGM-IL-7-hyFc, GMGMG-IL-7-hyFc, GMMMG-IL-7-hyFc, GGMGM-IL-7-hyFc, GGMMG-IL-7-hyFc, MGGMG-IL-7-hyFc, MGMGG-IL-7-hyFc, GMMGM-IL-7-hyFc, MGMMG-IL-7-hyFc, GMGGM-IL-7-hyFc, MMGMG-IL-7-hyFc, GMMGG-IL-7-hyFc, GMGGG-IL-7-hyFc, GGMGG-IL-7-hyFc, GGGMG-IL-7-hyFc or GGGGG-IL-7-hyFc was inserted into pAD15 expression vector. In order to insert a fusion protein gene into an expression vector pAD15, EcoRI site was generated at the 5'-end of the fusion protein gene sequence, and XbaI site was generated at the 3'-end of the hyFc gene sequence. Expression vector pAD15 was obtained from RcCMV backbone (available at Invitrogen, Carlsbad). The pAD15 contains a cytomegalovirus (CMV)-derived promoter, fetal bovine growth hormone-derived poly (A) sequence, rabbit beta globin-derived gIVS (globin intervening sequence) (*Mol Cell Biol.* 1988, 8: 4395), and other factors. The pAD15 vector was prepared by modifying various parts of RcCMV vector (Invitrogen). First, neomycin resistance site was removed by XhoI enzyme, and gIVS was added to the 3'-end of the CMV promoter region. In addition, mouse dihydrofolate reductase (DHFR) gene (GeneBank Accession No. NM 010049) was added to the 5'-end of the CMV promoter. In order to prepare the connection site between the 3'-end of IL-7 and the 5'-end of hyFc in the frame, NheI site was generated at the 3'-end of IL-7 coding sequence and the 5'-end of hyFc coding sequence. The final expression vector was prepared through a subcloning process using each restriction enzyme site. For more information regarding the preparation of the modified Fc region, U.S. Pat. No. 7,867,491 may be referred to(indicated as "hybrid (Fc) protein"). The hyFc protein of the present Example contains 9 amino acids of the C-terminal of IgD CH1 domain (90-98), 30 amino acids of IgD hinge region (133-162), 8 amino acids of the N-terminal of IgD CH2 domain (SHTQPLGV 163-170), 100 amino acids of IgG4 CH2 domain (121-220), and 107 amino acids of IgG4 CH3 domain (221-327).

Regarding the hyFc protein composed of a modified Fc region, the present invention takes reference to every preparation method for hFc-2, hFc-3, hFc-4, hFc-5 and hFc-6 described in the Example of the Korean Patent Publication No. 10-0897938. The hyFc protein used in the Examples of the present invention is a hybrid protein identical to hFc-5 described in the Korean Patent Publication No. 10-0897938.

PCR was carried out under the condition shown in Table 1. Denaturation, annealing and extension processes were carried out for 15 seconds at 98° C., for 30 seconds at 55° C., and for 60 seconds at 72° C., respectively.

TABLE 1

| | |
|---|---|
| pAD15 template comprising the gene of a modified IL-7 fusion protein | 2 μl |
| Forward primer (5'-accgaattcatgttccacgtgagcttcag-3') | 1.5 μl |
| Reverse primer (5'-ggttctagattagtgctccttggtgcccatc-3') | 1.5 μl |
| 5 × HF buffer | 20 μl |
| 2.5 mM dNTP | 8 μl |
| DMSO | 3 μl |
| Phusion (Thermo Scientific) | 1 μl |
| Tertiary distilled water | 64 μl |

The prepared expression vector, which is M-IL-7-hyFc, G-IL-7-hyFc, MM-IL-7-hyFc, MG-IL-7-hyFc, GM-IL-7-hyFc, GG-IL-7-hyFc, MMM-IL-7-hyFc, GMM-IL-7-hyFc, MGM-IL-7-hyFc, MMG-IL-7-hyFc, GGM-IL-7-hyFc, GMG-IL-7-hyFc, MGG-IL-7-hyFc, GGG-IL-7-hyFc, MMMM-IL-7-hyFc, GMMM-IL-7-hyFc, MGMM-IL-7-hyFc, MMGM-IL-7-hyFc, MMMG-IL-7-hyFc, GGMM-IL-7-hyFc, MGGM-IL-7-hyFc, MMGG-IL-7-hyFc, GMGM-IL-7-hyFc, MGMG-IL-7-hyFc, GMMG-IL-7-hyFc, GGGM-IL-7-hyFc, MGGG-IL-7-hyFc, GMGG-IL-7-hyFc, GGMG-IL-7-hyFc, GGGG-IL-7-hyFc, MMMMM-IL-7-hyFc, GMMMM-IL-7-hyFc, GGMMM-IL-7-hyFc, GGGMM-IL-7-hyFc, GGGGM-IL-7-hyFc, MGMMM-IL-7-hyFc, MGGMM-IL-7-hyFc, MGGGM-IL-7-hyFc, MGGGG-IL-7-hyFc, MMGMM-IL-7-hyFc, MMGGM-IL-7-hyFc, MMGGG-IL-7-hyFc, MMMGM-IL-7-hyFc, MMMGG-IL-7-hyFc, MMMMG-IL-7-hyFc, MGMGM-IL-7-hyFc, GMGMG-IL-7-hyFc, GMMMG-IL-7-hyFc, GGMGM-IL-7-hyFc, GGMMG-IL-7-hyFc, MGGMG-IL-7-hyFc, MGMGG-IL-7-hyFc, GMMGM-IL-7-hyFc, MGMMG-IL-7-hyFc, GMGGM-IL-7-hyFc, MMGMG-IL-7-hyFc, GMMGG-IL-7-hyFc, GMGGG-IL-7-hyFc, GGMGG-IL-7-hyFc, GGGMG-IL-7-hyFc or GGGGG-IL-7-hyFc, was transfected into CHO DG44 cells (from Dr.

Chasm, Columbia University, U.S.A.) by an electroporation method. After 48 hours, HT selection was carried out using 10% dFBS+MEM α medium without HT, and MTX amplification was carried out using HT selected clones to amplify the productivity. The obtained single cells were used for the preparation of a modified IL-7 fusion protein after testing the long-term stability thereof.

Example 2: Purification of Modified IL-7 Fusion Protein

After obtaining the culture solution containing the modified IL-7 fusion protein prepared by the method of Example 1, the productivity was measured by performing size-exclusion (SE) HPLC according to the conditions shown in Table 2 below. SE-HPLC was carried out for 40 minutes using TSK-GEL G3000WxL column.

First, each of the sample solutions of the modified IL-7 fusion protein was diluted with a buffer to a concentration of 1 mg/ml. Each diluent was filtered with 1 ml syringe and 0.2 μm filter and then put into an insert. The insert was inserted into a vial and the cap was kept closed. Then, each of the test solutions was injected into SE-HPLC system in an amount of 20 μl. The purity and relative productivity were measured based on the peak value.

As a result, the modified IL-7 fusion protein with the structure shown in FIG. 1, which has high productivity and purity, was purified (preparation and purification of the modified IL-7 fusion protein were carried out according to Korea Patent Application No. 10-2015-0082793).

Experimental Example 1: Selection of Basal Buffer 1.1. Selection Based on Thermodynamic Property To establish a formulation of the modified IL-7 fusion protein purified in Example 2 above, the thermodynamic property of the fusion proteins in three types of buffer was examined by differential scanning calorimetry (DSC) method.

First, the modified IL-7 fusion protein purified in Example 2 was subjected to dialysis at 4° C. using 20 mM histidine-acetate buffer or sodium citrate buffer with a pH of 5.0, 5.5, or 6.0, or tris buffer with a pH of 8.0.

Meanwhile, DSC was carried out using Microcal VP-DSC (Northampton, U.S.A.) having twin cells with the volume of 0.5147 cm$^3$ regarding the samples and a control solution. The scanning was conducted at the speed of 1.25° C./min at the temperature from 15° C. to 110° C. Before measuring the values, every solution was agitated in a vacuum state to remove air. Then, the standard value for a solution without the fusion protein was first determined, and the temperature record of a modified IL-7 fusion protein was shown by the values determined by subtracting the standard value from the measured values.

The resulting graph was shown by using Microcal LLC DSC (Northampton, U.S.A.) which was connected with Origin 7.0 software package provided with the device. In addition, from the results, the transition temperature (Tm) and enthalpy (ΔH) values of the fusion protein were obtained by using Origin 7.0 software.

Figure 2A:
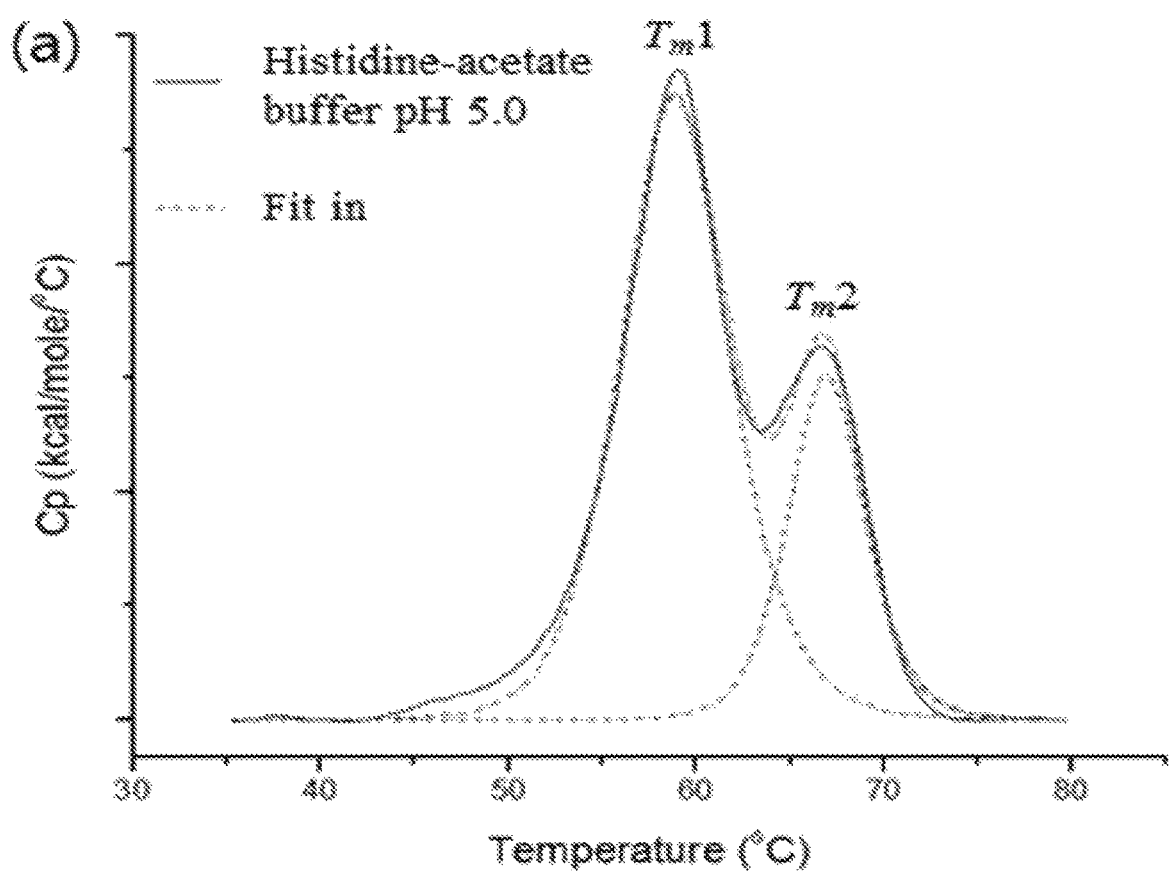
FIGS. 2A-2C present graphs showing the results of differential scanning calorimetry (DSC) of a modified IL-7 fusion protein under various basal buffer conditions.
Figure 2B:
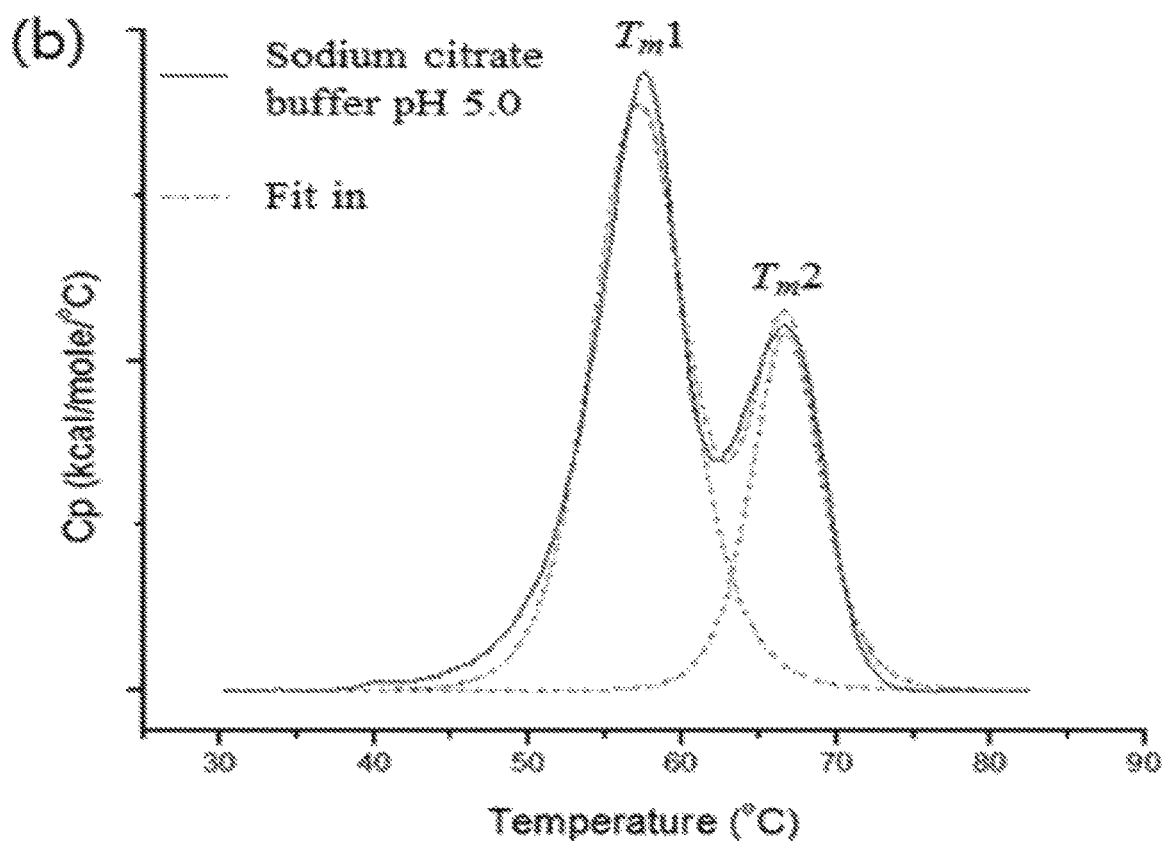
Figure 2C:
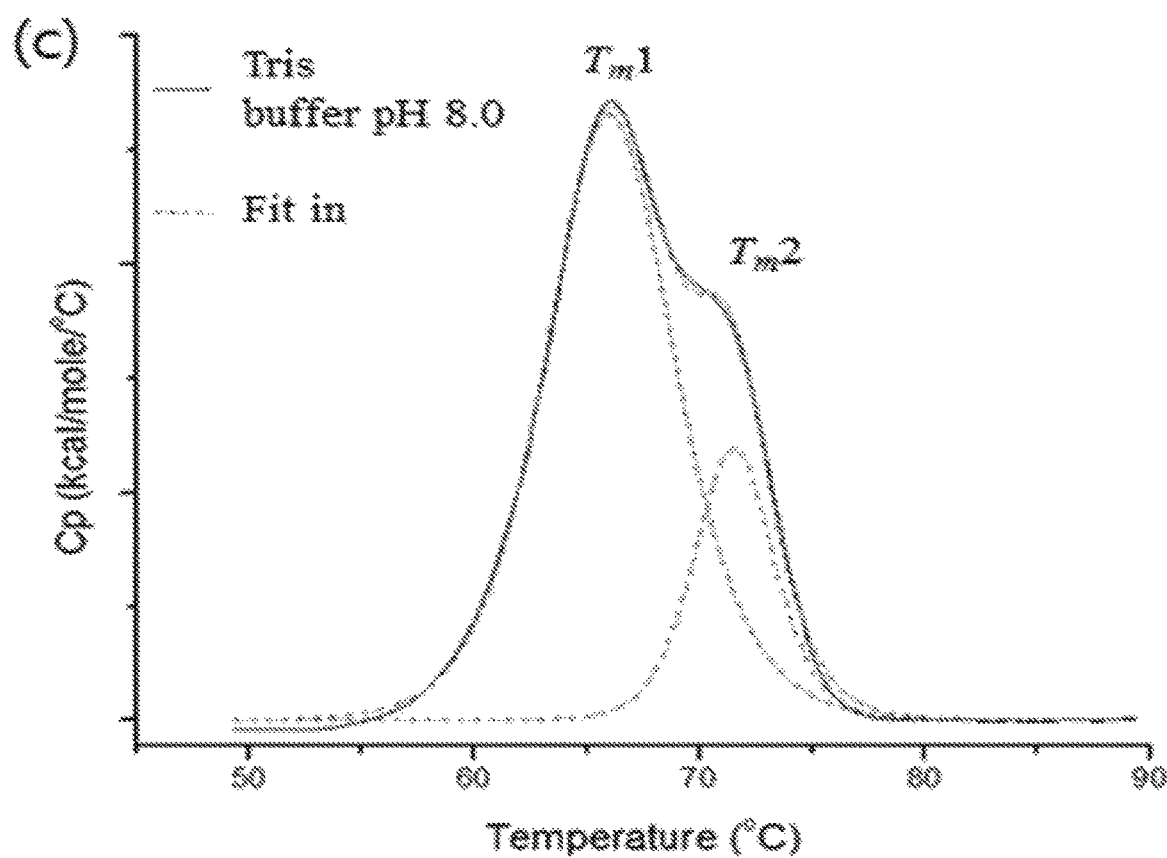

As shown in FIG. 2, in the case of MGM-IL-7-hyFc fusion protein, Tm 1 and Tm 2, the transition temperatures of IL-7 and hyFc, respectively, and two peaks representing the fusion protein structure unfolded by heat were identified in the typical DSC thermogram regarding the three types of buffers. These results indicate that each of IL-7 and hyFc exists in an unfolded state due to heat energy absorption, and they are structurally stable.

In general, hyFc is a design platform for the preparation of a long-acting protein in which IgD (hinge-$C_H2$) and IgG4 ($C_H2$-$C_H3$) are hybridized, and has single or double transitions from IgG4 according to various environmental factors. However, the result of the present experiment showed that apparently hyFc had a single transitional peak.

In addition, as shown in Table 2 below, Tm 1 and Tm 2 respectively increased from 58.89° C. to 62.92° C. and from 66.93° C. to 69.91° C., as the pH of the histidine-acetate buffer increased from 5.0 to 6.0. Moreover, ΔH also increased along with Tm. These results indicate that as pH increases, higher temperature and more heat energy are necessary for unfolding the structure of IL-7 and hyFc. That is, conformational stability of IL-7 and hyFc protein might increase as pH increases.

Even when sodium citrate with the pH of 5.0, 5.5, or 6.0 was used as a basal buffer, Tm 1 and Tm 2 increased as the pH increased, which results were identical to the results obtained by using a histidine-acetate buffer. It should be noted that Tm 1 and Tm 2, respectively, increased from 57.23° C. to 65.12° C. and from 66.74° C. to 71.34° C. as the pH increased from 5.0 to 6.0.

Regarding ΔH value when using sodium citrate as a basal buffer, ΔH values of Tm 1 and Tm 2 were the lowest when pH was 5.0. This result indicates that the suitable pH of a basal buffer for stably sustaining the structure of the fusion protein is 5.5 or 6.0.

When tris buffer of pH 8.0 was used, Tm 1, Tm 2 and ΔH value of Tm 1 were higher than those obtained with other buffers. This result was consistent with the aforementioned results which showed that the conformational stability of a modified IL-7 fusion protein increased as pH increased. In the case of tris buffer with a high pH, Tm 2 value increased compared to other buffers with a pH of 6.0, but the ΔH value of Tm 2 decreased, indicating that it might have bigger influence on the conformational stability of IL-7 than on the stability of hyFc.

TABLE 2

| Buffer/pH (MGM-IL-7-hyFc concentration, mg/ml) | | Transition temperature (° C.) | | Enthalpy (kJ/mol) | |
|---|---|---|---|---|---|
| | | Tm 1 | Tm 2 | ΔH1 | ΔH2 |
| Histidine-acetate | pH 5.0 (8.6) | 58.89 | 66.93 | 263.47 | 102.91 |
| | pH 5.5 (8.8) | 61.11 | 68.72 | 290.68 | 104.17 |
| | pH 6.0 (8.6) | 62.92 | 69.91 | 332.06 | 115.41 |
| Sodium citrate | pH 5.0 (9.3) | 57.23 | 66.74 | 242.15 | 110.48 |
| | pH 5.5 (9.6) | 62.17 | 70.28 | 305.27 | 124.77 |
| | pH 6.0 (9.8) | 65.12 | 71.34 | 292.10 | 126.19 |
| Tris | pH 8.0 (7.8) | 71.53 | 66.06 | 384.27 | 104.58 |

1.2. Selection by Dynamic Light Scattering (DLS) Analysis

DLS analysis was carried out in order to evaluate the electrostatic interaction between proteins, and Z-average size, polydispersity index (PDI) and zeta potential, and the effect of pH and a buffer on the aggregates formation. The particle size of the protein and zeta potential were measured using Zetasizer Nano ZS90 (Malvern Instruments, UK).

Z-average size refers to the average of elements such as a fragment, a monomer and an aggregate, which is very sensitive to even small changes such as the presence of a small aggregate portion. If the measured PDI value is lower than 0.05, it is shown as a monodisperse standard, and if the value is higher than 0.7, it indicates that the sample has a wide size distribution. Zeta potential is an electrical repulsion of proteins surrounding a hydrodynamic surface. If the absolute value of the zeta potential is high, the protein is less subject to aggregation and instability in a solution.

First, for the DLS analysis, a modified IL-7 fusion protein sample was equilibrated at the measurement temperature of 10° C. Using 1 ml of the sample, particle size was measured 5 times in a disposable sizing cuvette, and zeta potential was measured 3 times in a disposable capillary cell with the angle fixed to 90°. Intensity of the peak, average particle size, PDI and the zeta potential were calculated using Zetasizer software version 7.11 (Malvern Instruments, UK), which was provided with the device.

Figure 3A:
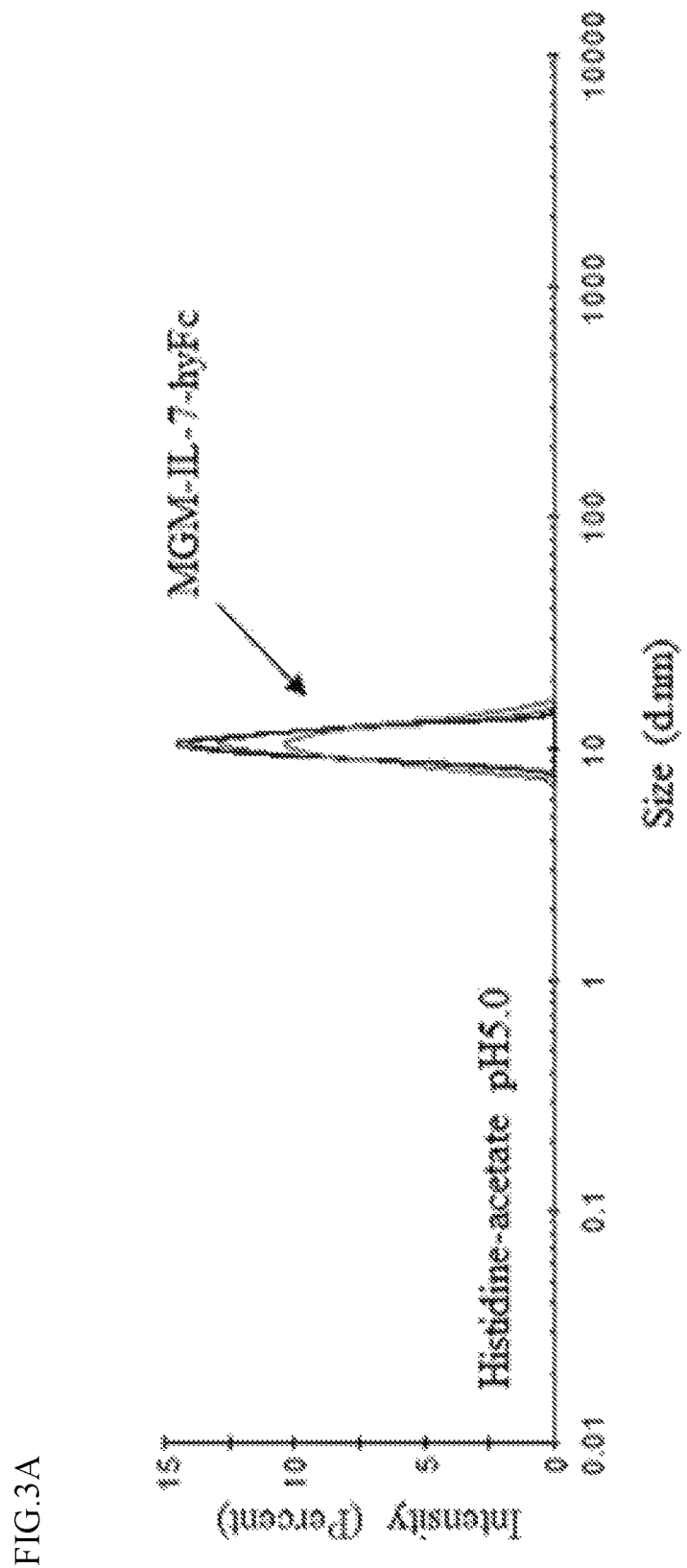
FIGS. 3A-3C present graphs showing the results of dynamic light scattering (DLS) analysis of a modified IL-7 fusion protein under various basal buffer conditions.
Figure 3B:
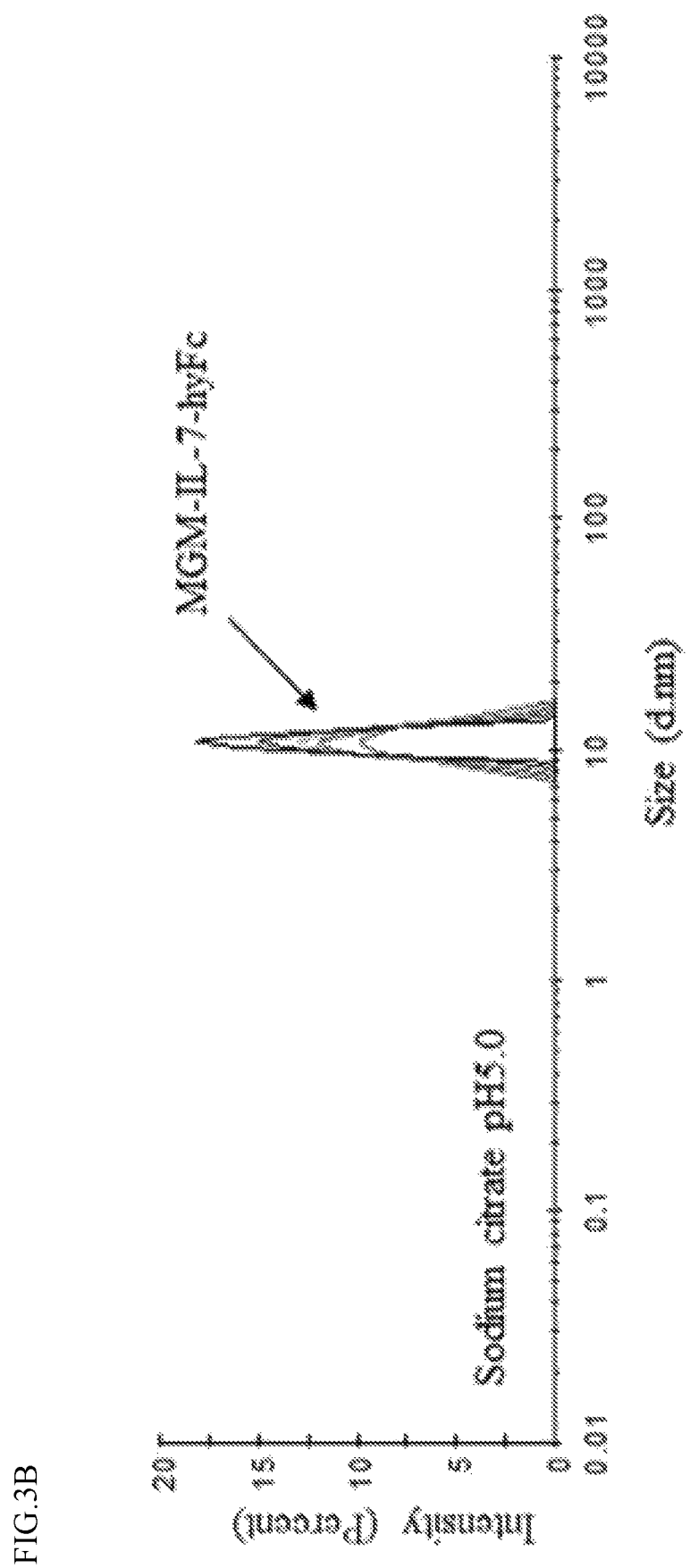
Figure 3C:
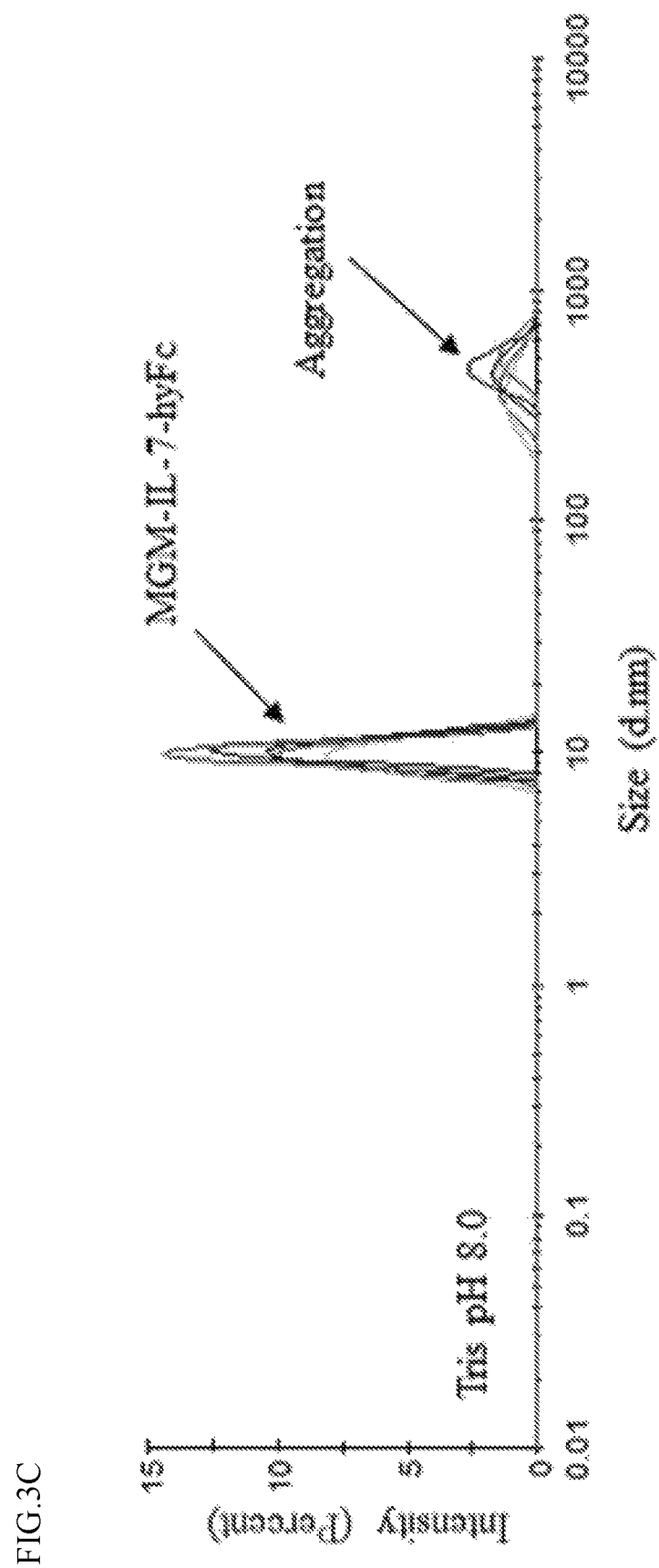

The protein size distribution represented by the intensity of protein peaks when using histidine-acetate or sodium citrate of pH 5.0, or tris of pH 8.0 as a basal buffer was shown in FIG. 3. The Z-average size, PDI and zeta potential of the three buffers in different pH conditions were shown in Table 3.

As shown in FIG. 3, when histidine-acetate or sodium citrate of pH 5.0 was used as a basal buffer, the resulting graph showed a single narrow peak throughout 5 consecutive measurements. Meanwhile, when tris buffer of pH 8.0 was used, a new peak was identified, which suggested aggregation at 100 to 1,000 nm.

As shown in Table 3, when histidine-acetate was used as a basal buffer, new aggregation appeared as pH increased from 5.0 to 6.0, and the Z-average size and PDI, respectively, increased from 10.43 nm to 10.64 nm, and 0.02 to 0.07. In addition, as pH increased, the absolute value of zeta potential decreased from 4.42 to 1.28.

The aggregation phenomenon according to the pH change as described above was also observed when sodium citrate was used as a basal buffer: that is, Z-average size and PDI increased and zeta potential decreased in a sodium citrate basal buffer.

However, Z-average size and PDI in a tris basal buffer highly increased to 12.38 nm and 0.34, respectively, as compared to those in other buffers. In addition, protein aggregation took place in the tris basal buffer. Also, even though aggregation took place, the absolute value of zeta potential in the tris buffer was 20.27, which was higher than those in other buffers.

Therefore, in order to reduce the aggregation of the modified IL-7 fusion protein of the present invention, histidine-acetate or sodium citrate may be suitable as a basal buffer, preferably in the pH condition with low zeta potential. In a high pH condition, the buffer can be used in combination with protein aggregation inhibitor.

TABLE 3

| Buffer/pH (MGM-IL-7-hyFc concentration, mg/ml) | | Z-average size (d · nm*) | PDI | Absolute value of zeta potential (mV) |
|---|---|---|---|---|
| Histidine-acetate | pH 5.0 (8.6) | 10.43 ± 0.06 | 0.02 ± 0.01 | 4.42 ± 0.32 |
| | pH 5.5 (8.8) | 10.58 ± 0.09 | 0.03 ± 0.02 | 1.11 ± 0.43 |
| | pH 6.0 (8.6) | 10.64 ± 0.24 | 0.07 ± 0.05 | 1.28 ± 0.47 |
| Sodium citrate | pH 5.0 (9.3) | 10.73 ± 0.09 | 0.02 ± 0.01 | 5.18 ± 0.74 |
| | pH 5.5 (9.6) | 10.82 ± 0.10 | 0.03 ± 0.02 | 3.38 ± 0.57 |
| | pH 6.0 (9.8) | 11.03 ± 0.17 | 0.08 ± 0.03 | 2.46 ± 0.42 |
| Tris | pH 8.0 (7.8) | 12.38 ± 0.84 | 0.34 ± 0.05 | 20.27 ± 0.42 |

*d · nm: diameter in nanometer

Experimental Example 2: Selection of Excipients 2.1. Selection According to the Protective Effect on Stress Conditions In order to examine the protective effect of excipients against stress environments such as agitation and oxidation, various excipients including a surfactant with a concentration of 5 w/v %, a sugar with a concentration of 5 w/v % and an amino acid with a concentration of 50 mM, were subjected to a size-exclusion chromatography. In the control group, only modified IL-7 fusion protein was added to a basal buffer. For the basal buffer, histidine-acetate or sodium citrate basal buffer of pH 5.0 was used.

Specifically, the modified IL-7 fusion proteins were dialyzed at 4° C. with the solutions prepared by adding various types of excipients to histidine-acetate or sodium citrate basal buffers of pH 5.0. For the agitation stress environment, 0.5 ml of the modified IL-7 fusion protein as dialyzed was put into a microtube, which was then put into a box and agitated for 2 hours at room temperature using Vortex-Genie 2 (Scientific Industries, Inc., U.S.A.) at strength 7.

Meanwhile, for the oxidation stress environment, 0.5 ml of the dialyzed MGM-IL-7-hyFc fusion protein was added with hydrogen peroxide to the final concentration of 1.0% (v/v) and stored for 20 hours at room temperature. Size-exclusion chromatography was carried out using high performance liquid chromatography (HPLC) system (Waters e2695, U.S.A.) at the UV wavelength of 214 nm of absorption spectrum.

<HPLC Condition>
Column: TSKgel G3000SWXL SEC column (300×7.8 mm) (TOSOH Bioscience, U.S.A.)
Mobile phase: solution containing 100 mM NaCl and 10% acetonitrile in 50 mM sodium phosphate (pH 6.8)
Flow rate: 0.5 ml/min As a result, several elements including water-soluble aggregation, monomers and fragments were observed, and the content of each element was calculated by the mathematical equation 1.

$$\% \text{ content of specific element} = C_t/C_s \times 100 \quad \text{[Equation 1]}$$

Herein, Ct refers to the area of each element (water-soluble aggregation, monomer and fragment), and Cs refers the sum of the peaks of the elements when a sample is obtained.

As a result, as shown in Tables 4 and 5, the monomer content in a sodium citrate buffer in the control group was 96.34%, which decreased to 78.18% by agitation and 48.16% by oxidation.

It was found that MGM-IL-7-hyFc fusion protein was protected from the agitation stress by adding widely-known non-ionic surfactant such as Tween or poloxamer to a histidine-acetate or sodium citrate buffer. Such non-ionic surfactants have an excellent effect of protecting the protein from uncoiling in a hydrophobic interface. When Twin 20, Twin 80 or poloxamer 188 were added to a buffer, the monomer content did not significantly decrease. However, the protective effects of these surfactants were substantially similar, indicating that the surfactants protected the fusion protein of the present invention in a hydrophobic environment which constantly changes due to agitation.

Meanwhile, the surfactants did not show any protective effect on MGM-IL-7-hyFc fusion protein against oxidation stress, but rather caused more reduction of the monomer content than the control group. Moreover, Twin 20 and Twin 80 are known to oxidate a protein. Poloxamer 188 also made the fusion protein of the present invention unstable in the oxidation condition, as Twin 20 and Twin 80 did.

A sugar or a sugar alcohol such as sucrose and sorbitol is often used as a pharmaceutical excipient for stabilizing MGM-IL-7-hyFc fusion protein. However, sucrose and sorbitol caused lower monomer content than the control group, which indicated that they do not have a protective effect on the fusion protein of the present invention against agitation stress.

After agitation in the sodium citrate buffer, based on the reference value not exposed to a stress, the monomer content decreased by 18.16% in the control group, while the monomer contents decreased by 39.29% and 53.51% when sucrose and sorbitol, respectively, were added. Meanwhile, after agitation in the histidine-acetate buffer, based on the reference value not exposed to a stress, the monomer content decreased by 2.23% in the control group, while the monomer contents decreased by 11.53% and 13.77% when sucrose and sorbitol, respectively, were added.

It is known that the addition of a sugar and a sugar alcohol to a formulation stimulates aggregates formation of IgG during agitation. When sucrose or sorbitol were added to a formulation, the aggregates formation increased during agitation, which led to the decrease in the stability of MGM-IL-7-hyFc fusion protein, irrespective of the kind of a basal buffer.

Meanwhile, sucrose and sorbitol increased the stability of a fusion protein under the oxidation stress. In a sodium citrate buffer, the monomer content decreased by 48.18% in the control group based on the reference value not exposed to a stress, while the monomer contents decreased by 2.55% and 2.79% when sucrose and sorbitol, respectively, were added. Similarly, in a histidine-acetate buffer, the monomer content decreased by 35.36% in the control group based on the reference value not exposed to a stress, while the monomer contents decreased by 1.68% and 1.47% when sucrose and sorbitol, respectively, were added. This result indicates that sucrose and sorbitol have a protective effect on protein from oxidation. The two substances are reported to be able to stabilize a protein by preferential exclusion from a surface of a protein.

Next, with regard to the effect of an amino acid on the stability of MGM-IL-7-hyFc fusion protein under a stress condition, the protective effect against agitation was very low when 50 mM arginine, glutamate, glycine and histidine amino acids were respectively added to sodium citrate buffers. The monomer content decreased by 18.16% in the control group based on the reference value not exposed to a stress, while the monomer contents decreased by 49.71%, 64.75%, 3.96% and 46.75% when arginine, glutamate, glycine and histidine were, respectively, added. Meanwhile, arginine and glutamate were found to make a fusion protein of the present invention unstable when histidine-acetate buffer was used.

Meanwhile, when glycine was added to a histidine-acetate buffer, the monomer content of the MGM-IL-7-hyFc fusion protein did not decrease as compared to the reference value not exposed to a stress. The result was conflicting to the result from a sodium citrate buffer, suggesting that the stability of MGM-IL-7-hyFc fusion protein can change depending on the environmental factors including a buffer and an excipient.

Moreover, the protective effect against oxidation stress was observed when arginine and glycine were respectively added to sodium citrate buffers, but such effect was not observed when they were added to histidine-acetate buffers. However, with regard to the oxidation stress, when arginine and glycine were respectively added to sodium citrate buffers, the samples showed decreases of 30.66% and 3.21% respectively in the monomer contents based on the reference value not exposed to a stress, which were smaller than in the control group (decreased by 48.18%). Meanwhile, when arginine and glycine were added to histidine-acetate buffers, the monomer contents decreased significantly by 39.34% and 37.90% respectively based on the reference value not exposed to a stress, compared to the control group (decreased by 35.36%). Especially, in both types of buffers, the addition of glycine showed a protective effect on the fusion protein of the present invention against agitation and oxidation stresses depending on buffer types, and the addition of glutamate resulted in an excellent protective effect on the fusion protein against oxidation stress.

TABLE 4

| | | Sodium citrate pH 5.0 [MGM-IL-7-hyFc concentration: 9.5 mg/ml (Final concentration 3.0 mg/ml)] | | | | | | | | |
|---|---|---|---|---|---|---|---|---|---|---|
| | | Aggregate (%) | | | Monomer (%) | | | Fragment (%) | | |
| Excipient | | Reference* | Agitation | Oxidation | Reference* | Agitation | Oxidation | Reference* | Agitation | Oxidation |
| Control group | | 0.81 | 20.58 | 47.98 | 96.34 | 78.18 | 48.16 | 2.85 | 1.24 | 3.86 |
| Sugar & Sugar alcohol | Sucrose | 0.69 | 41.78 | 0.65 | 95.65 | 56.36 | 93.10 | 3.66 | 1.86 | 6.25 |
| | Sorbitol | 0.57 | 55.79 | 0.98 | 96.08 | 42.57 | 93.29 | 3.34 | 1.64 | 5.74 |
| Surfactant | Tween 20 | 0.57 | 0.84 | 48.13 | 95.74 | 95.77 | 48.02 | 3.69 | 3.39 | 3.85 |
| | Tween 80 | 0.69 | 0.64 | 48.02 | 95.76 | 95.80 | 47.34 | 3.55 | 3.56 | 4.63 |
| | Poloxamer 188 | 0.69 | 0.74 | 50.17 | 95.71 | 95.68 | 46.45 | 3.60 | 3.58 | 3.38 |
| Amino acid | Arginine | 0.75 | 52.65 | 31.39 | 95.62 | 45.91 | 64.96 | 3.36 | 1.44 | 3.65 |
| | Glutamate | 0.55 | 67.66 | 0.81 | 95.60 | 30.85 | 93.73 | 3.85 | 1.48 | 5.46 |
| | Glycine | 0.69 | 34.09 | 2.44 | 95.76 | 64.80 | 92.55 | 3.55 | 1.11 | 5.01 |
| | Histidine | 0.77 | 50.34 | 22.37 | 95.70 | 48.95 | 73.53 | 3.53 | 0.72 | 4.10 |

*Note:
Not exposed to a stress

TABLE 5

Histidine-acetate pH 5.0 [MGM-IL-7-hyFc concentration: 9.5 mg/ml (Final concentration 3.0 mg/ml)]

| | | Aggregate (%) | | | Monomer (%) | | | Fragment (%) | | |
|---|---|---|---|---|---|---|---|---|---|---|
| Excipient | | Reference* | Agitation | Oxidation | Reference* | Agitation | Oxidation | Reference* | Agitation | Oxidation |
| Control group | | 0.45 | 4.52 | 35.03 | 95.39 | 93.16 | 60.03 | 4.16 | 2.33 | 4.94 |
| Sugar & | Sucrose | 0.42 | 13.71 | 0.52 | 95.62 | 84.09 | 93.94 | 3.96 | 2.20 | 5.54 |
| Sugar alcohol | Sorbitol | 0.46 | 15.80 | 0.37 | 95.74 | 81.97 | 94.27 | 3.80 | 2.23 | 5.36 |
| Surfactant | Tween 20 | 0.43 | 0.55 | 39.36 | 95.32 | 95.73 | 56.59 | 4.25 | 3.72 | 4.06 |
| | Tween 80 | 0.36 | 0.60 | 40.93 | 96.00 | 95.30 | 55.29 | 3.64 | 4.10 | 3.79 |
| | Poloxamer 188 | 0.50 | 0.64 | 41.89 | 95.77 | 95.87 | 54.37 | 3.73 | 3.49 | 3.75 |
| Amino acid | Arginine | 0.51 | 29.11 | 39.35 | 96.04 | 69.26 | 56.70 | 3.45 | 1.63 | 3.95 |
| | Glutamate | 0.42 | 56.11 | 0.77 | 96.22 | 39.40 | 93.87 | 3.36 | 1.50 | 5.36 |
| | Glycine | 0.53 | 2.93 | 38.42 | 95.55 | 94.83 | 57.65 | 3.92 | 2.24 | 3.93 |

*Note:
Not exposed to a stress 2.2. Selection by DLS Analysis

To examine the effect of various excipients including a surfactant, a sugar and an amino acid on the stability of a modified IL-7 fusion protein, DLS analysis was conducted by the method described in Experimental Example 1.2. The measurements of a particle size and zeta potential were carried out three times, respectively.

Z-average size of MGM-IL-7-hyFc fusion proteins which were exposed to the agitation and oxidation stress in sodium citrate buffer with pH 5.0 was shown in FIG. 4 and Table 6.

TABLE 6

Sodium citrate pH 5.0

| | | Reference* | | Agitation | | Oxidation | |
|---|---|---|---|---|---|---|---|
| Excipient | | Z-average size (d · nm) | PDI | Z-average size (d · nm) | PDI | Z-average size (d · nm) | PDI |
| Control group | | 11.29 | 0.07 | 19.40 | 0.19 | 177.10 | 0.85 |
| Sugar & | Sucrose | 11.80 | 0.17 | — | — | 13.07 | 0.28 |
| Sugar alcohol | Sorbitol | 11.89 | 0.14 | — | — | 14.11 | 0.32 |
| Surfactant | Tween 20 | 10.61 | 0.07 | 10.77 | 0.11 | — | — |
| | Tween 80 | 10.69 | 0.03 | 10.78 | 0.07 | — | — |
| | Poloxamer 188 | 11.01 | 0.05 | 11.32 | 0.11 | — | — |
| Amino acid | Glutamate | 11.09 | 0.06 | — | — | 11.26 | 0.06 |
| | Glycine | 11.65 | 0.13 | — | — | 50.71 | 0.58 |

*Note:
Not exposed to a stress

Figure 4A:
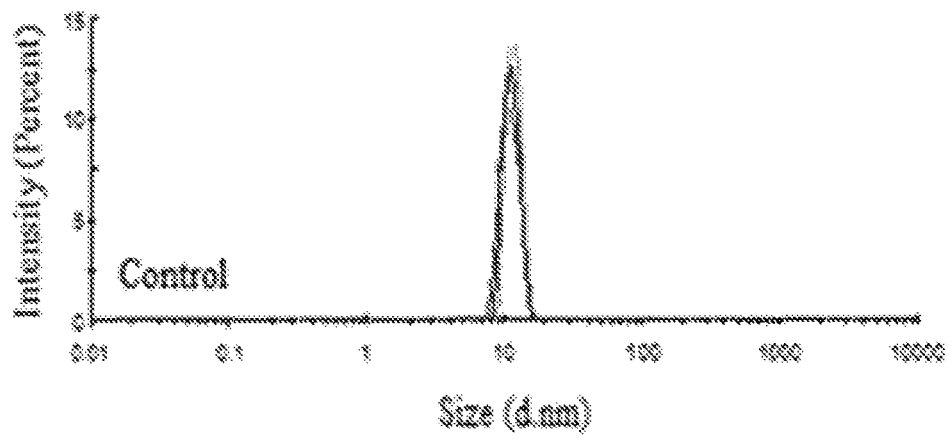
FIGS. 4A-4C present graphs showing the results of DLS analysis of a modified IL-7 fusion protein under the conditions in which various excipients were added to a histidine-acetate buffer.
Figure 4A:
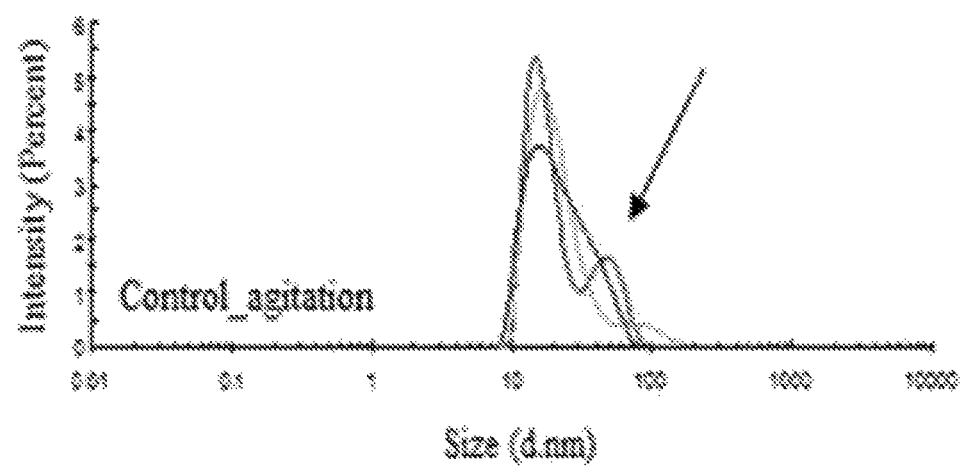
Figure 4A:
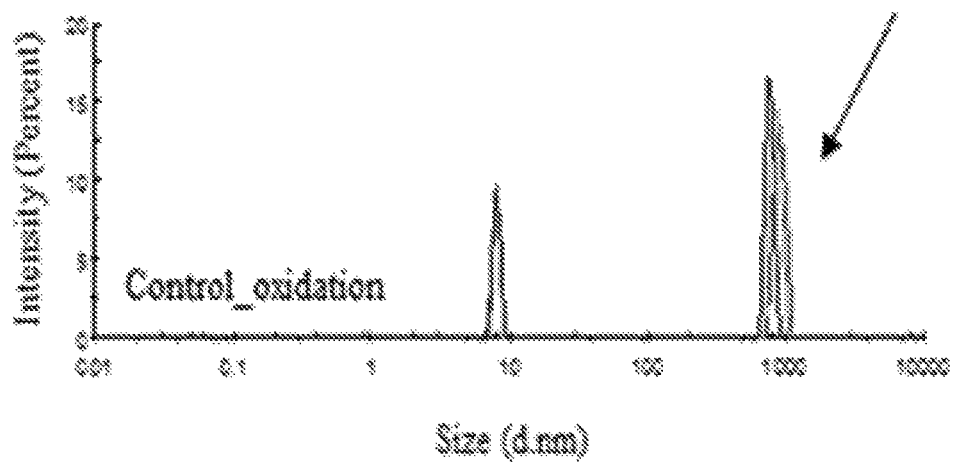
Figure 4B:
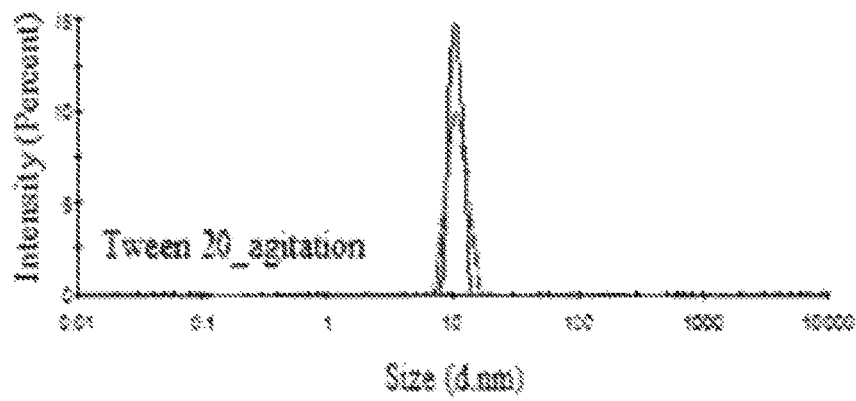
Figure 4B:
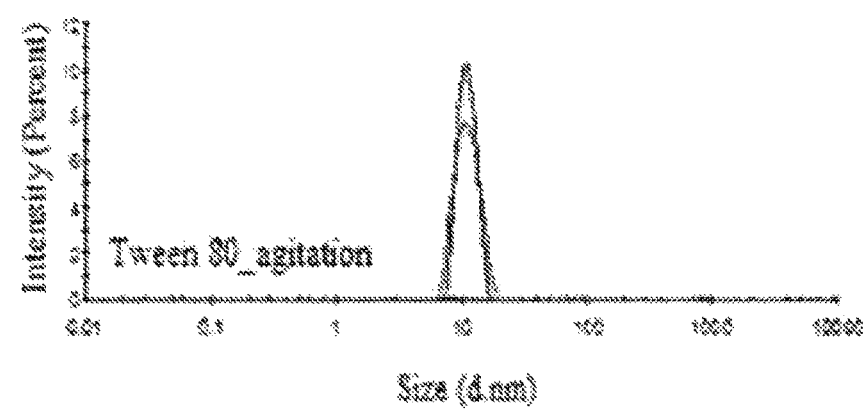
Figure 4B:
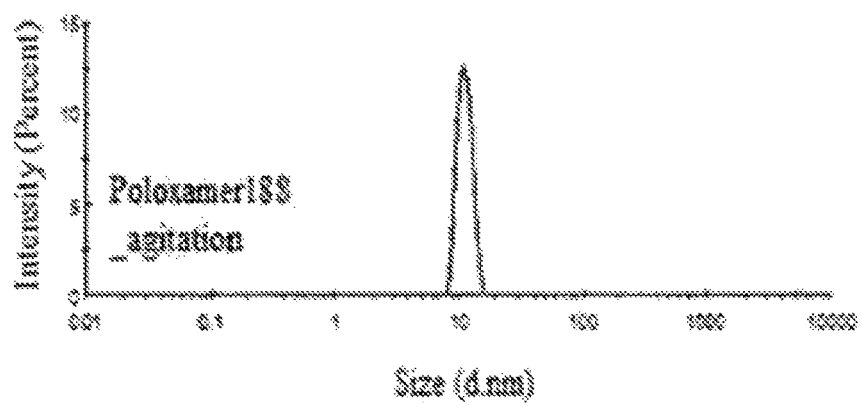

As shown in FIG. 4a, the control group showed only a single narrow peak in the particle size measurement which was conducted three times. However, the agitation control group, which was exposed to an agitation stress, showed another peak at the size of 100 nm (see arrow in the middle graph of FIG. 4a). In this control group, Z-average size increased from 11.29 nm to 19.40 nm, and PDI also increased from 0.07 to 0.19, indicating that an aggregation formation took place. Meanwhile, when Twin 20, Twin 80 and poloxamer 188 were added, Z-average size increased by 0.16, 0.09, 0.31 nm, respectively, and PDI increased by 0.04, 0.04 and 0.06, respectively. The increase in Z-average size and PDI implies that the aggregation is induced by agitation. A smaller increase was observed by the addition of a surfactant, indicating that the surfactants had a protein protective effect from aggregates formation. As shown in FIG. 4b, an aggregate peak was not observed when a surfactant was added.

Figure 4C:
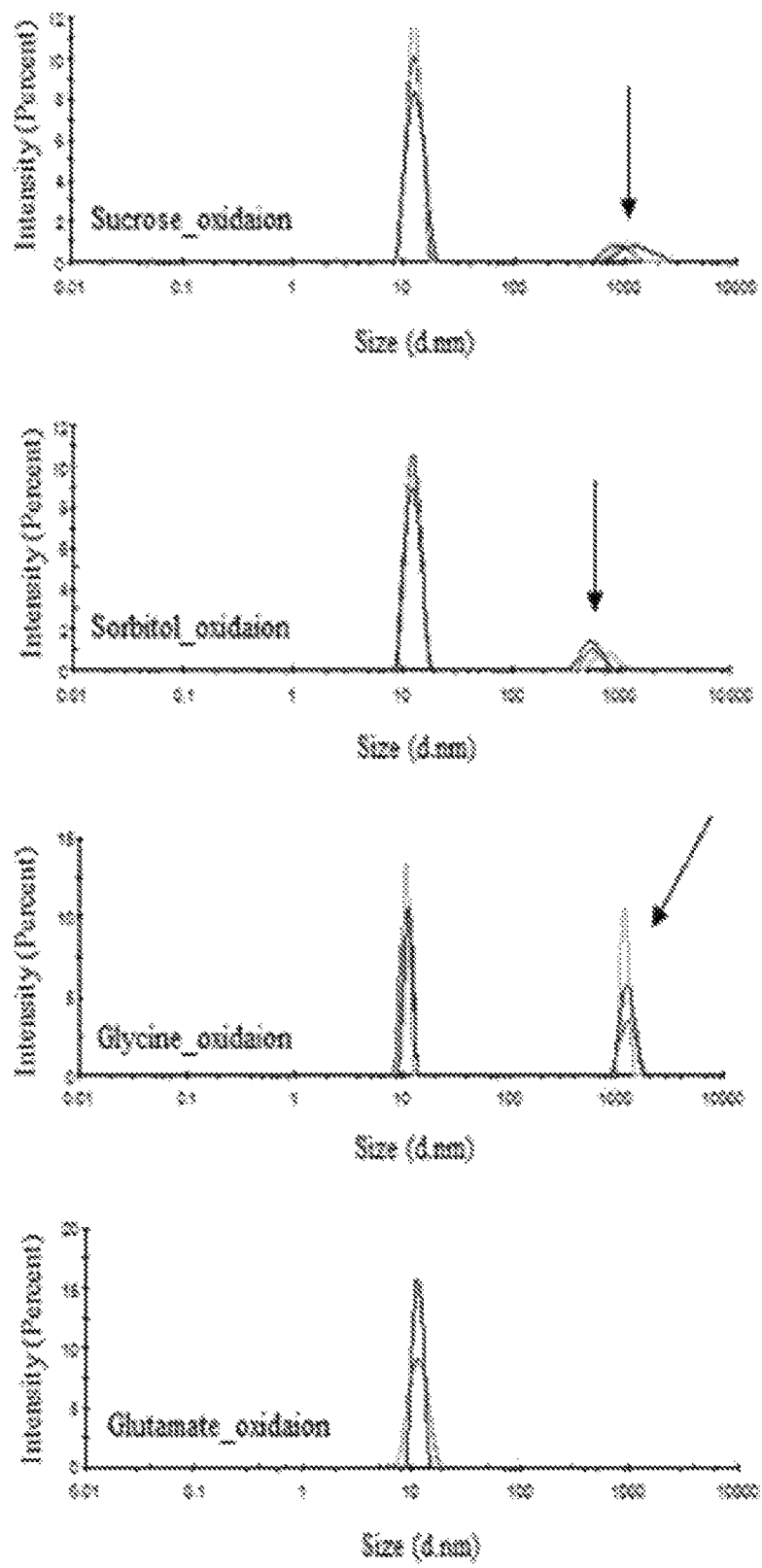

The oxidation control group, which was exposed to an oxidation stress, showed an additional peak at the size of 1,000 nm (see arrow in the bottom graph of FIG. 4a), while Z-average size and PDI increased from 11.29 nm to 177.10 nm, and 0.07 to 0.85 nm, respectively. This result indicates that an aggregate is formed by oxidation, and the formed aggregate is bigger than that formed by agitation. As shown in FIG. 4c, an aggregate peak was also observed when sucrose, sorbitol and glycine were respectively added (see arrows), but aggregates were not formed when glutamate was added. In the case of glutamate-added sample, Z-average size increased by 0.17 nm and PDI did not change. This result indicates that when glutamate is added to sodium citrate buffer with pH 5.0, it shows an excellent protective effect on MGM-IL-7-hyFc fusion protein against oxidation stress. Meanwhile, when sucrose, sorbitol and glycine were added, Z-average size increased by 1.27 nm, 2.22 nm and 39.06 nm, respectively, and PDI increased by 0.11, 0.18 and 0.45, respectively, which were considered to be small when compared to the samples in which other excipients were added. This result indicates that sucrose, sorbitol and glycine have a protective effect on the fusion protein of the present invention against oxidation stress, which is consistent with the result of Experimental Example 2.1.

Meanwhile, the Z-average size of MGM-IL-7-hyFc fusion proteins which were exposed to agitation and oxidation stress in histidine-acetate buffer with pH 5.0 was shown in FIG. 5 and Table 7.

TABLE 7

| | | Histidine-acetate pH 5.0 | | | | | |
|---|---|---|---|---|---|---|---|
| | | Reference* | | Agitation | | Oxidation | |
| Excipient | | Z-average size (d · nm) | PDI | Z-average size (d · nm) | PDI | Z-average size (d · nm) | PDI |
| Control group | | 10.50 | 0.02 | 11.70 | 0.10 | 17.43 | 0.37 |
| Sugar & | Sucrose | 11.21 | 0.17 | — | — | 12.47 | 0.22 |
| Sugar alcohol | Sorbitol | 12.02 | 0.13 | — | — | 11.61 | 0.09 |
| Surfactant | Tween 20 | 10.66 | 0.10 | 10.79 | 0.12 | — | — |
| | Tween 80 | 10.40 | 0.03 | 10.50 | 0.03 | — | — |
| | Poloxamer 188 | 10.83 | 0.04 | 10.74 | 0.07 | — | — |
| Amino acid | Glutamate | 10.90 | 0.04 | — | — | 11.31 | 0.06 |
| | Glycine | 10.68 | 0.03 | 15.66 | 0.41 | — | — |

*Note:
Not exposed to a stress

Figure 5A:
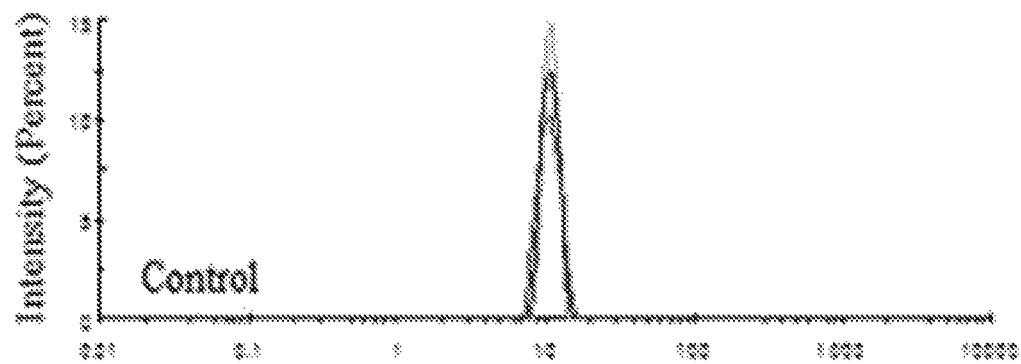
FIGS. 5A-5C present graphs showing the results of DLS analysis of a modified IL-7 fusion protein under the conditions in which various excipients were added to a sodium citrate buffer.
Figure 5A:
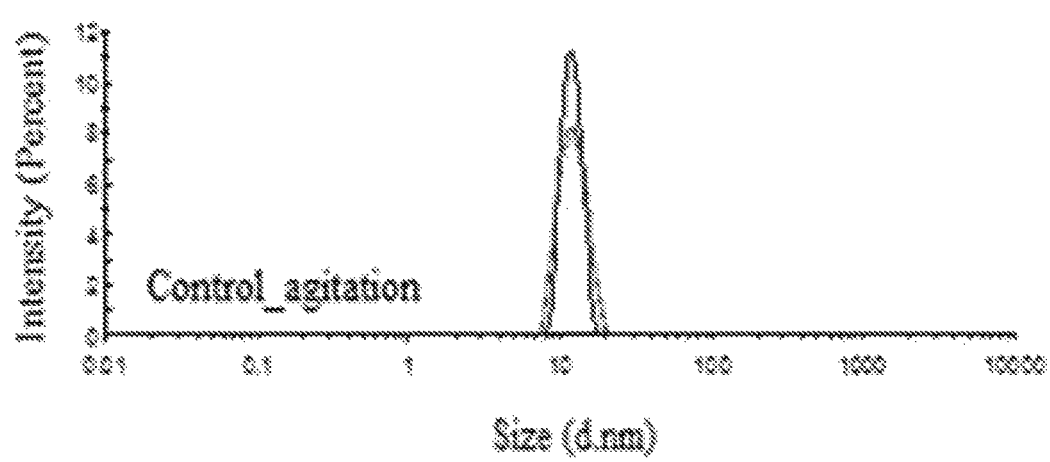
Figure 5A:
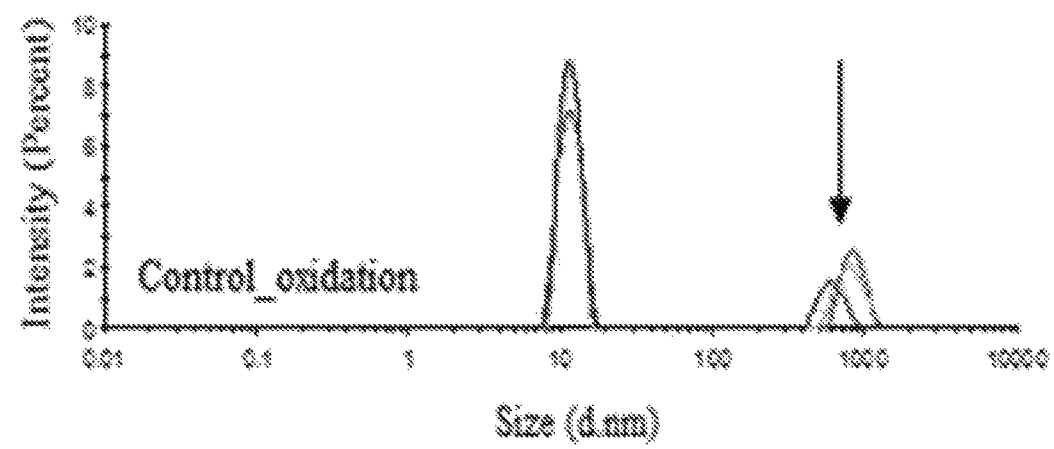
Figure 5B:
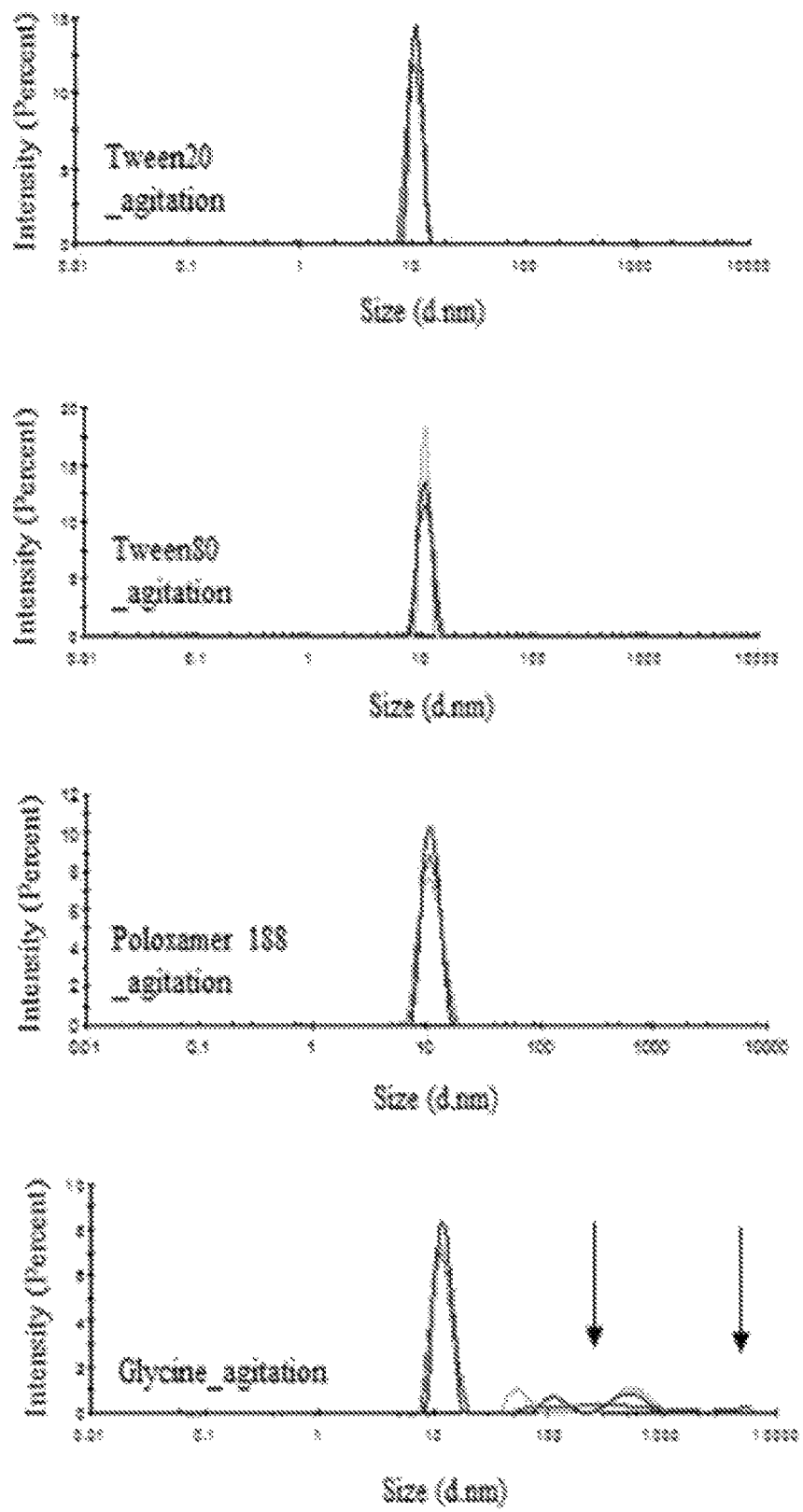

As shown in FIG. 5a, the control group and the agitation control group showed a single narrow peak, which is a different result from the agitation control group with the sodium citrate buffer (see arrow in bottom graph). However, as shown in FIG. 5b, an aggregate peak was observed when glycine was added (see arrows in bottom graph), but an aggregate peak was not observed and Z-average size and PDI did not change when surfactants such as Twin 20, Twin 80 and poloxamer 188 were added. This result indicates that an aggregates formation can take place by agitation when glycine is added to a MGM-IL-7-hyFc fusion protein formulation.

Figure 5C:
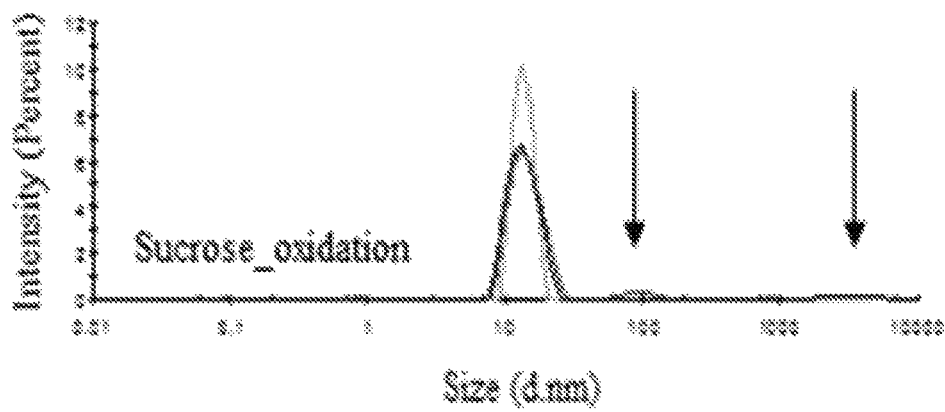
Figure 5C:
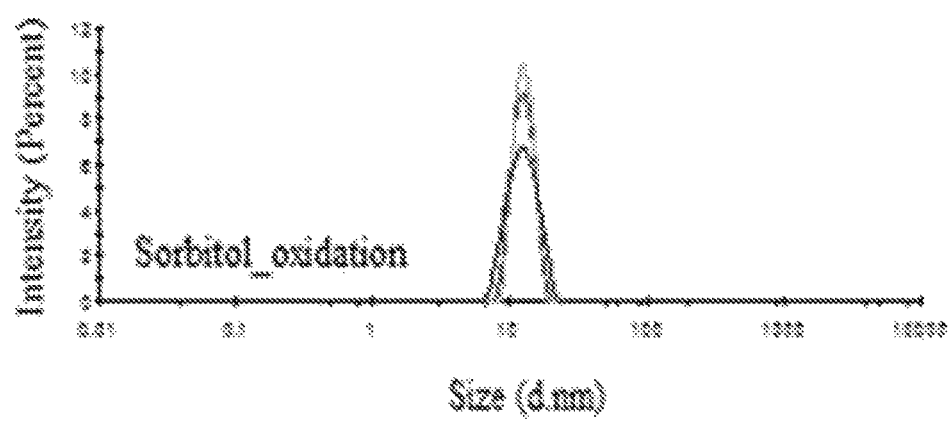
Figure 5C:
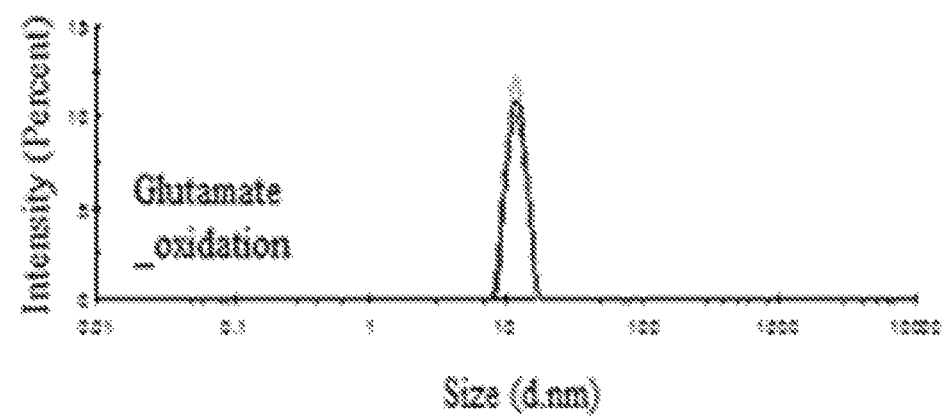

As shown in FIG. 5c, when sucrose was added, Z-average size and PDI, respectively, increased from 11.21 nm to 12.47 nm, and 0.17 to 0.22 by oxidation (see arrows in top graph). Both of the changes were smaller than the control group, indicating that sucrose has a protein protective effect against oxidation stress, but cause the problem of aggregates formation. Meanwhile, when sorbitol was added, Z-average size and PDI respectively decreased from 12.02 nm to 11.61 nm, and 0.13 to 0.09, while no aggregate peak was found. The decreases in Z-average size and PDI suggest the increase of fragments, even if not significant. When glutamate was added, Z-average size and PDI increased slightly, while neither aggregates nor fragments were found.

Therefore, it was found that the surfactants such as Twin 20, Twin 80 and poloxamer 188 have a protective effect on the fusion protein of the present invention against oxidation or agitation stress; a sugar or a sugar alcohol such as sucrose and sorbitol exhibits a protective effect against oxidation stress; and amino acids show different effects according to the basal buffer, but overall, glutamate shows a high protective effect.

Experimental Example 3: Combination of Excipients

From the results of Experimental Example 2, Tween 80 and sucrose were selected as the excipients showing a protective effect on the modified IL-7 fusion protein against agitation and oxidation stresses, respectively. For experiment for the combination of these two excipients, Design of Experiment software (Design-Expert, Stat-Ease Inc., U.S.A.) was used. The two excipients were combined as shown in Table 8, and the effect thereof on stability of the modified IL-7 fusion protein was examined. Stress condition in the present Experimental Example was the same as Experimental Example 2.1., and the final concentration of the modified IL-7 fusion protein in the formulation was adjusted to 3 to 100 mg/ml.

TABLE 8

| | Excipient (Addition concentration w/v %) | |
|---|---|---|
| | Tween 80 | Sucrose |
| 1 | 0.00 | 0 |
| 2 | 0.05 | 0 |
| 3 | 0.10 | 0 |
| 4 | 0.00 | 2.5 |
| 5 | 0.05 | 2.5 |
| 6 | 0.10 | 2.5 |
| 7 | 0.00 | 5 |
| 8 | 0.05 | 5 |
| 9 | 0.10 | 5 |
| 10 | 0.05 | 2.5 |

To examine the protective effect against a stress condition, size-exclusion chromatography was carried out [at 214 nm of UV wavelength of absorption spectrum using high performance liquid chromatography (HPLC) system (Waters e2695, U.S.A.)], under the same HPLC condition as Experimental Example 2.1.

First, an experiment was conducted regarding a formulation comprising the modified IL-7 fusion protein in a concentration of 3 mg/ml. As a result, as shown in Table 9, the control group with sodium citrate buffer showed a monomer content of 95.65%, which decreased to 74.77% by agitation, and to 49.81% by oxidation. The samples in which Tween 80 was added showed a protective effect against agitation stress, while those in which sucrose was added showed a protective effect against oxidation stress. The samples in which Tween 80 and sucrose were added in combination showed the protective effect against agitation stress and oxidation stress.

TABLE 9

| Basal Buffer | Sample | Excipient | | Final concentration (w/v %) | | SE-HPLC (%) | | |
|---|---|---|---|---|---|---|---|---|
| | | | | | | Reference* | Agitation | Oxidation |
| Sodium citrate | 1 | Tween 80 | Sucrose | 0.00 | 0 | 95.65 | 74.77 | 49.81 |
| | 2 | Tween 80 | Sucrose | 0.05 | 0 | 95.06 | 95.39 | 48.88 |
| | 3 | Tween 80 | Sucrose | 0.10 | 0 | 95.39 | 95.28 | 50.51 |
| | 4 | Tween 80 | Sucrose | 0.00 | 2.5 | 94.42 | 71.26 | 92.24 |
| | 5 | Tween 80 | Sucrose | 0.05 | 2.5 | 95.08 | 95.19 | 91.93 |
| | 6 | Tween 80 | Sucrose | 0.10 | 2.5 | 95.06 | 95.85 | 91.68 |
| | 7 | Tween 80 | Sucrose | 0.00 | 5 | 95.29 | 71.70 | 92.67 |
| | 8 | Tween 80 | Sucrose | 0.05 | 5 | 95.51 | 95.02 | 91.96 |
| | 9 | Tween 80 | Sucrose | 0.10 | 5 | 95.42 | 95.27 | 92.49 |
| | 10 | Tween 80 | Sucrose | 0.05 | 2.5 | 94.96 | 95.30 | 91.71 |

*Note:
Not exposed to a stress

Meanwhile, as shown in Table 10, the control group with histidine-acetate buffer showed a monomer content of 95.46%, which decreased to 93.60% by agitation, and to 50.63% by oxidation. As compared to the sodium citrate buffer, the histidine-acetate buffer showed more excellent protective effect against agitation stress, and the protective effects of the added excipients was similar to those in the samples with sodium citrate.

TABLE 10

| Basal buffer | Sample | Excipient | | Final concentration (w/v %) | | SE-HPLC (%) | | |
|---|---|---|---|---|---|---|---|---|
| | | | | | | Reference* | Agitation | Oxidation |
| Histidine-acetate | 1 | Tween 80 | Sucrose | 0.00 | 0 | 95.46 | 93.60 | 50.63 |
| | 2 | Tween 80 | Sucrose | 0.05 | 0 | 95.77 | 94.62 | 50.68 |
| | 3 | Tween 80 | Sucrose | 0.10 | 0 | 95.35 | 95.30 | 50.59 |
| | 4 | Tween 80 | Sucrose | 0.00 | 2.5 | 95.49 | 94.93 | 93.23 |
| | 5 | Tween 80 | Sucrose | 0.05 | 2.5 | 95.52 | 94.36 | 92.32 |
| | 6 | Tween 80 | Sucrose | 0.10 | 2.5 | 95.75 | 94.82 | 91.43 |
| | 7 | Tween 80 | Sucrose | 0.00 | 5 | 95.34 | 94.86 | 93.66 |
| | 8 | Tween 80 | Sucrose | 0.05 | 5 | 95.29 | 94.90 | 93.36 |
| | 9 | Tween 80 | Sucrose | 0.10 | 5 | 95.38 | 94.42 | 93.58 |
| | 10 | Tween 80 | Sucrose | 0.05 | 2.5 | 94.90 | 94.90 | 92.12 |

From the results, the condition of the excipients was selected. To acquire the proper osmotic strength of an injection, sorbitol and mannitol were further added, and agitation stress and oxidation stress experiments were conducted, and additional experiment under the condition of adding 1.5 w/v % sorbitol was also conducted.

As a candidate formulation for each of sodium citrate buffer and histidine-acetate buffer, 5 w/v % sucrose, 1.5 w/v % sorbitol, and 0.05 w/v % Tween 80 were added to the formulations for MGM-IL-7-hyFc fusion protein. Using the above formulations, freeze/thaw, temperature stress and oxidation stress experiments were conducted. The stress conditions are shown in Table 11, and the analysis result is shown in Table 12.

TABLE 11

| Stress condition | |
|---|---|
| Condition | Stress method |
| Control group | −80° C. |
| Freeze/thaw | −80° C.→Room temperature (5 times) |
| Temperature | 37° C. (39 h, 3 day), 50° C. (20 h) |
| Oxidation | 0.1% or 1% $H_2O_2$, room temperature 20 h |

TABLE 12

| Basal buffer | pH Before stress exposure | Osmotic pressure Before stress exposure | SE-HPLC (%) Before stress exposure | Freeze/thaw | 37° C., 39 h | 50° C., 20 h | 0.1% $H_2O_2$ | 1% $H_2O_2$ |
|---|---|---|---|---|---|---|---|---|
| 20 mM Sodium citrate, 5 w/v % Sucrose, 1.5 w/v % Sorbitol, 0.05 w/v % Tween 80, pH 5.0 | 5.02 | 303 | 95.76 | 95.77 | 94.83 | 93.81 | 95.71 | 92.86 |
| 20 mM Histidine-acetate, 5 w/v % Sucrose, 1.5 w/v % Sorbitol, 0.05 w/v % Tween 80, pH 5.0 | 4.98 | 300 | 95.59 | 95.64 | 95.41 | 95.47 | 95.95 | 93.83 |

As a result of the stress test using the candidate formulations, as shown in Table 12, in this case where a sodium citrate buffer is used, the control group showed a monomer content of 95.76%, and about 3% of change by stress was observed.

In the case where a histidine-acetate buffer is used, the control group showed a monomer content of 95.59%, and about 1% of change by stress was observed, showing a slightly better protective effect compared to the sodium citrate buffer.

The effect of the candidate formulations on the modified IL-7 fusion protein of various concentrations was examined. First, a formulation comprising 3 to 100 mg/ml modified IL-7 fusion protein, 20 mM sodium citrate, and 5 w/v % sucrose was prepared. Then, 1 to 2 w/v % sorbitol or mannitol as a sugar alcohol, and 0.05 w/v % Tween 80 or poloxamer as a surfactant were added thereto, and the final pH was adjusted to 5.0. The result indicated that, 3 to 100 mg/ml of modified IL-7 fusion protein was well protected under the various combination conditions.

What is claimed is:

1. A pharmaceutical formulation comprising: (a) an interleukin-7 (IL-7) fusion protein, which comprises an IL-7 protein which is conjugated to a Fc region of an immunoglobulin; (b) a basal buffer with a concentration of 10 to 50 mM; (c) a sugar with a concentration of 2.5 to 5 w/v %; and (d) a surfactant with a concentration of 0.05 to 6 w/v %; wherein the IL-7 fusion protein further comprises an oligopeptide selected from the group consisting of M, G, MM, MG, GM, GG, MMM, GMM, MGM, MMG, GGM, GMG, MGG, GGG, MMMM (SEQ ID NO: 9), GMMM (SEQ ID NO: 10), MGMM (SEQ ID NO: 11), MMGM (SEQ ID NO: 12), MMMG (SEQ ID NO: 13), GGMM (SEQ ID NO: 14), MGGM (SEQ ID NO: 15), MMGG (SEQ ID NO: 16), GMGM (SEQ ID NO: 17), MGMG (SEQ ID NO: 18), GMMG (SEQ ID NO: 19), GGGM (SEQ ID NO: 20), MGGG (SEQ ID NO: 21), GMGG (SEQ ID NO: 22), GGMG (SEQ ID NO: 23), GGGG (SEQ ID NO: 24), MMMMM (SEQ ID NO: 25), GMMMM (SEQ ID NO: 26), GGMMM (SEQ ID NO: 27), GGGMM (SEQ ID NO: 28), GGGGM (SEQ ID NO: 29), MGMMM (SEQ ID NO: 30), MGGMM (SEQ ID NO: 31), MGGGM (SEQ ID NO: 32), MGGGG (SEQ ID NO: 33), MMGMM (SEQ ID NO: 34), MMGGM (SEQ ID NO: 35), MMGGG (SEQ ID NO: 36), MMMGM (SEQ ID NO: 37), MMMGG (SEQ ID NO: 38), MMMMG (SEQ ID NO: 39), MGGGM (SEQ ID NO: 40), MGMGM (SEQ ID NO: 41), GMGMG (SEQ ID NO: 42), GMMMG (SEQ ID NO: 43), GGMGM (SEQ ID NO: 44), GGMMG (SEQ ID NO: 45), MGGMG (SEQ ID NO: 46), MGMGG (SEQ ID NO: 47), GMMGM (SEQ ID NO: 48), MGMMG (SEQ ID NO: 49), GMGGM (SEQ ID NO: 50), MMGMG (SEQ ID NO: 51), GMMGG (SEQ ID NO: 52), GMGGG (SEQ ID NO: 53), GGMGG (SEQ ID NO: 54), GGGMG (SEQ ID NO: 55), and GGGGG (SEQ ID NO: 56); wherein the IL-7 protein comprises: (i) amino acid residues 26-177 of the sequence set forth in SEQ ID NO: 1, (ii) amino acid residues 26-154 of the sequence set forth in SEQ ID NO: 2, (iii) amino acid residues 26-154 of the sequence set forth in SEQ ID NO: 3, (iv) amino acid residues 26-8177 of the sequence set forth in SEQ ID NO: 4, (v) amino acid residues 26-176 of the sequence set forth in SEQ ID NO: 5, or (iv) amino acid residues 26-176 of the sequence set forth in SEQ ID NO:6; and wherein the Fc region of the immunoglobulin has the amino acid sequence set forth in SEQ ID NO: 7.

2. The pharmaceutical formulation of claim 1, wherein the oligopeptide is bound to the N-terminal of the IL-7 protein.

3. The pharmaceutical formulation of claim 1, wherein the Fc region of the immunoglobulin is bound to the C-terminal of the IL-7 protein.

4. The pharmaceutical formulation of claim 1, wherein the basal buffer is histidine-acetate or sodium citrate.

5. The pharmaceutical formulation of claim 1, wherein the sugar is selected from the group consisting of sucrose, trehalose, dextrose, and a mixture thereof.

6. The pharmaceutical formulation of claim 1, wherein the surfactant is selected from the group consisting of polysorbate, polyoxyethylene alkyl ether, polyoxyethylene stearate, alkyl sulfates, polyvinyl pyridone, poloxamer and a mixture thereof.

7. The pharmaceutical formulation of claim 1, further comprising any one amino acid selected from the group consisting of arginine, glutamate, glycine, histidine, and a mixture thereof.

8. The pharmaceutical formulation of claim 7, wherein the concentration of the amino acid ranges from 40 to 60 mM.

9. The pharmaceutical formulation of claim 8, wherein the concentration of the amino acid is 50 mM.

10. The pharmaceutical formulation of claim 1, further comprising a sugar alcohol, wherein the sugar alcohol is at a concentration of 1 to 2 w/v %.

11. The pharmaceutical formulation of claim 10, wherein the sugar alcohol is selected from the group consisting of sorbitol, xylitol, maltitol, mannitol, and a mixture thereof.

12. The pharmaceutical formulation of claim 1, wherein the pH of the formulation is 5.0.

13. The pharmaceutical formulation of claim 1, wherein the formulation is a liquid formulation.

14. The pharmaceutical formulation of claim 1, wherein the IL-7 protein comprises amino acid residues 26-178 of the sequence set forth in SEQ ID NO: 1.

15. The pharmaceutical formulation of claim 1, wherein the formulation does not comprise any one amino acid selected from the group consisting of arginine, glutamate, glycine, histidine, and a mixture thereof.

16. The pharmaceutical formulation of claim 15, wherein the formulation does not comprise histidine.

17. The pharmaceutical formulation of claim 1, wherein the oligopeptide is bound to the N-terminal of the IL-7 protein and the Fc region of the immunoglobulin is bound to the C-terminal of the IL-7 protein.

18. The pharmaceutical formulation of claim 1, wherein the IL-7 fusion protein comprises the amino acid sequence set forth in SEQ ID NO: 8.

19. The pharmaceutical formulation of claim 18, wherein: (a) the basal buffer is histidine-acetate or sodium citrate; (b) the sugar is selected from the group consisting of sucrose, trehalose, dextrose, and a mixture thereof; (c) wherein the surfactant is selected from the group consisting of polysorbate, polyoxyethylene alkyl ether, polyoxyethylene stearate, alkyl sulfates, polyvinyl pyridone, poloxamer and a mixture thereof; (d) an amino acid selected from the group consisting of arginine, glutamate, glycine, histidine, and a mixture thereof; (e) a sugar alcohol; or (f) any combination of (a) to (e).

20. The pharmaceutical formulation of claim 19, wherein: (a) the amino acid is present at a concentration of 40 to 60 mM; (b) the sugar alcohol is at a concentration of 1 to 2 w/v %; (c) the pH is 5.0; or (d) any combination of (a) to (c).

* * * * *

```
                      SEQUENCE LISTING

Sequence total quantity: 56
SEQ ID NO: 1             moltype = AA  length = 177
FEATURE                  Location/Qualifiers
source                   1..177
                         mol_type = protein
                         note = amino acid sequence of human IL-7 (Accession number
                           : P13232)
                         organism = synthetic construct
SEQUENCE: 1
MFHVSFRYIF GLPPLILVLL PVASSDCDIE GKDGKQYESV LMVSIDQLLD SMKEIGSNCL   60
NNEFNFFKRH ICDANKEGMF LFRAARKLRQ FLKMNSTGDF DLHLLKVSEG TTILLNCTGQ  120
VKGRKPAALG EAQPTKSLEE NKSLKEQKKL NDLCFLKRLL QEIKTCWNKI LMGTKEH     177

SEQ ID NO: 2             moltype = AA  length = 154
FEATURE                  Location/Qualifiers
source                   1..154
                         mol_type = protein
                         note = amino acid sequence of rat IL-7 (Accession number :
                           P56478)
                         organism = synthetic construct
SEQUENCE: 2
MFHVSFRYIF GIPPLILVLL PVTSSDCHIK DKDGKAFGSV LMISINQLDK MTGTDSDCPN   60
NEPNFFKKHL CDDTKEAAFL NRAARKLRQF LKMNISEEFN DHLLRVSDGT QTLVNCTSKE  120
EKTIKEQKKN DPCFLKRLLR EIKTCWNKIL KGSI                              154

SEQ ID NO: 3             moltype = AA  length = 154
FEATURE                  Location/Qualifiers
source                   1..154
                         mol_type = protein
                         note = amino acid sequence of mouse IL-7 (Accession number
                           : P10168)
                         organism = synthetic construct
SEQUENCE: 3
MFHVSFRYIF GIPPLILVLL PVTSSECHIK DKEGKAYESV LMISIDELDK MTGTDSNCPN   60
NEPNFFRKHV CDDTKEAAFL NRAARKLRQF LKMNISEEFN VHLLTVSQGT QTLVNCTSKE  120
EKNVKEQKKN DACFLKRLLR EIKTCWNKIL KGSI                              154

SEQ ID NO: 4             moltype = AA  length = 177
FEATURE                  Location/Qualifiers
source                   1..177
                         mol_type = protein
                         note = amino acid sequence of monkey IL-7 (Accession number
                           : NP_001279008)
                         organism = synthetic construct
```

```
SEQUENCE: 4
MFHVSFRYIF GLPPLILVLL PVASSDCDIE GKDGKQYESV LMVSIDQLLD SMKEIGSNCL    60
NNEFNFFKRH LCDDNKEGMF LFRAARKLKQ FLKMNSTGDF DLHLLKVSEG TTILLNCTGK   120
VKGRKPAALG EPQPTKSLEE NKSLKEQKKL NDSCFLKRLL QKIKTCWNKI LMGTKEH      177

SEQ ID NO: 5            moltype = AA  length = 176
FEATURE                 Location/Qualifiers
source                  1..176
                        mol_type = protein
                        note = amino acid sequence of cow IL-7 (Accession number :
                          P26895)
                        organism = synthetic construct
SEQUENCE: 5
MFHVSFRYIF GIPPLILVLL PVASSDCDIS GKDGGAYQNV LMVNIDDLDN MINFDSNCLN    60
NEPNFFKKHS CDDNKEASFL NRASRKLRQF LKMNISDDFK LHLSTVSQGT LTLLNCTSKG   120
KGRKPPSLSE AQPTKNLEEN KSSKEQKKQN DLCFLKILLQ KIKTCWNKIL RGIKEH       176

SEQ ID NO: 6            moltype = AA  length = 176
FEATURE                 Location/Qualifiers
source                  1..176
                        mol_type = protein
                        note = amino acid sequence of sheep IL-7 (Accession number
                          : Q28540)
                        organism = synthetic construct
SEQUENCE: 6
MFHVSFRYIF GIPPLILVLL PVASSDCDFS GKDGGAYQNV LMVSIDDLDN MINFDSNCLN    60
NEPNFFKKHS CDDNKEASFL NRAARKLKQF LKMNISDDFK LHLSTVSQGT LTLLNCTSKG   120
KGRKPPSLGE AQPTKNLEEN KSLKEQRKQN DLCFLKILLQ KIKTCWNKIL RGITEH       176

SEQ ID NO: 7            moltype = AA  length = 245
FEATURE                 Location/Qualifiers
source                  1..245
                        mol_type = protein
                        note = amino acid sequence of hyFc
                        organism = synthetic construct
SEQUENCE: 7
RNTGRGGEEK KKEKEKEEQE ERETKTPECP SHTQPLGVFL FPPKPKDTLM ISRTPEVTCV    60
VVDVSQEDPE VQFNWYVDGV EVHNAKTKPR EEQFNSTYRV VSVLTVLHQD WLNGKEYKCK   120
VSNKGLPSSI EKTISKAKGQ PREPQVYTLP PSQEEMTKNQ VSLTCLVKGF YPSDIAVEWE   180
SNGQPENNYK TTPPVLDSDG SFFLYSRLTV DKSRWQEGNV FSCSVMHEAL HNHYTQKSLS   240
LSLGK                                                               245

SEQ ID NO: 8            moltype = AA  length = 400
FEATURE                 Location/Qualifiers
source                  1..400
                        mol_type = protein
                        note = amino acid sequence of modified IL-7(MGM) fused hyFc
                        organism = synthetic construct
SEQUENCE: 8
MGMDCDIEGK DGKQYESVLM VSIDQLLDSM KEIGSNCLNN EFNFFKRHIC DANKEGMFLF    60
RAARKLRQFL KMNSTGDFDL HLLKVSEGTT ILLNCTGQVK GRKPAALGEA QPTKSLEENK   120
SLKEQKKLND LCFLKRLLQE IKTCWNKILM GTKEHRNTGR GGEEKKKEKE KEEQEERETK   180
TPECPSHTQP LGVFLFPPKP KDTLMISRTP EVTCVVVDVS QEDPEVQFNW YVDGVEVHNA   240
KTKPREEQFN STYRVVSVLT VLHQDWLNGK EYKCKVSNKG LPSSIEKTIS KAKGQPREPQ   300
VYTLPPSQEE MTKNQVSLTC LVKGFYPSDI AVEWESNGQP ENNYKTTPPV LDSDGSFFLY   360
SRLTVDKSRW QEGNVFSCSV MHEALHNHYT QKSLSLSLGK                         400

SEQ ID NO: 9            moltype = AA  length = 4
FEATURE                 Location/Qualifiers
source                  1..4
                        mol_type = protein
                        note = oligopeptides conjugated with IL-7
                        organism = synthetic construct
SEQUENCE: 9
MMMM                                                                  4

SEQ ID NO: 10           moltype = AA  length = 4
FEATURE                 Location/Qualifiers
source                  1..4
                        mol_type = protein
                        note = oligopeptides conjugated with IL-7
                        organism = synthetic construct
SEQUENCE: 10
GMMM                                                                  4

SEQ ID NO: 11           moltype = AA  length = 4
FEATURE                 Location/Qualifiers
source                  1..4
                        mol_type = protein
```

```
                            note = oligopeptides conjugated with IL-7
                            organism = synthetic construct
SEQUENCE: 11
MGMM                                                                          4

SEQ ID NO: 12               moltype = AA  length = 4
FEATURE                     Location/Qualifiers
source                      1..4
                            mol_type = protein
                            note = oligopeptides conjugated with IL-7
                            organism = synthetic construct
SEQUENCE: 12
MMGM                                                                          4

SEQ ID NO: 13               moltype = AA  length = 4
FEATURE                     Location/Qualifiers
source                      1..4
                            mol_type = protein
                            note = oligopeptides conjugated with IL-7
                            organism = synthetic construct
SEQUENCE: 13
MMMG                                                                          4

SEQ ID NO: 14               moltype = AA  length = 4
FEATURE                     Location/Qualifiers
source                      1..4
                            mol_type = protein
                            note = oligopeptides conjugated with IL-7
                            organism = synthetic construct
SEQUENCE: 14
GGMM                                                                          4

SEQ ID NO: 15               moltype = AA  length = 4
FEATURE                     Location/Qualifiers
source                      1..4
                            mol_type = protein
                            note = oligopeptides conjugated with IL-7
                            organism = synthetic construct
SEQUENCE: 15
MGGM                                                                          4

SEQ ID NO: 16               moltype = AA  length = 4
FEATURE                     Location/Qualifiers
source                      1..4
                            mol_type = protein
                            note = oligopeptides conjugated with IL-7
                            organism = synthetic construct
SEQUENCE: 16
MMGG                                                                          4

SEQ ID NO: 17               moltype = AA  length = 4
FEATURE                     Location/Qualifiers
source                      1..4
                            mol_type = protein
                            note = oligopeptides conjugated with IL-7
                            organism = synthetic construct
SEQUENCE: 17
GMGM                                                                          4

SEQ ID NO: 18               moltype = AA  length = 4
FEATURE                     Location/Qualifiers
source                      1..4
                            mol_type = protein
                            note = oligopeptides conjugated with IL-7
                            organism = synthetic construct
SEQUENCE: 18
MGMG                                                                          4

SEQ ID NO: 19               moltype = AA  length = 4
FEATURE                     Location/Qualifiers
source                      1..4
                            mol_type = protein
                            note = oligopeptides conjugated with IL-7
                            organism = synthetic construct
SEQUENCE: 19
GMMG                                                                          4

SEQ ID NO: 20               moltype = AA  length = 4
FEATURE                     Location/Qualifiers
```

-continued

```
source                  1..4
                        mol_type = protein
                        note = oligopeptides conjugated with IL-7
                        organism = synthetic construct
SEQUENCE: 20
GGGM                                                                    4

SEQ ID NO: 21           moltype = AA  length = 4
FEATURE                 Location/Qualifiers
source                  1..4
                        mol_type = protein
                        note = oligopeptides conjugated with IL-7
                        organism = synthetic construct
SEQUENCE: 21
MGGG                                                                    4

SEQ ID NO: 22           moltype = AA  length = 4
FEATURE                 Location/Qualifiers
source                  1..4
                        mol_type = protein
                        note = oligopeptides conjugated with IL-7
                        organism = synthetic construct
SEQUENCE: 22
GMGG                                                                    4

SEQ ID NO: 23           moltype = AA  length = 4
FEATURE                 Location/Qualifiers
source                  1..4
                        mol_type = protein
                        note = oligopeptides conjugated with IL-7
                        organism = synthetic construct
SEQUENCE: 23
GGMG                                                                    4

SEQ ID NO: 24           moltype = AA  length = 4
FEATURE                 Location/Qualifiers
source                  1..4
                        mol_type = protein
                        note = oligopeptides conjugated with IL-7
                        organism = synthetic construct
SEQUENCE: 24
GGGG                                                                    4

SEQ ID NO: 25           moltype = AA  length = 5
FEATURE                 Location/Qualifiers
source                  1..5
                        mol_type = protein
                        note = oligopeptides conjugated with IL-7
                        organism = synthetic construct
SEQUENCE: 25
MMMMM                                                                   5

SEQ ID NO: 26           moltype = AA  length = 5
FEATURE                 Location/Qualifiers
source                  1..5
                        mol_type = protein
                        note = oligopeptides conjugated with IL-7
                        organism = synthetic construct
SEQUENCE: 26
GMMMM                                                                   5

SEQ ID NO: 27           moltype = AA  length = 5
FEATURE                 Location/Qualifiers
source                  1..5
                        mol_type = protein
                        note = oligopeptides conjugated with IL-7
                        organism = synthetic construct
SEQUENCE: 27
GGMMM                                                                   5

SEQ ID NO: 28           moltype = AA  length = 5
FEATURE                 Location/Qualifiers
source                  1..5
                        mol_type = protein
                        note = oligopeptides conjugated with IL-7
                        organism = synthetic construct
SEQUENCE: 28
GGGMM                                                                   5
```

| | | |
|---|---|---|
| SEQ ID NO: 29<br>FEATURE<br>source | moltype = AA   length = 5<br>Location/Qualifiers<br>1..5<br>mol_type = protein<br>note = oligopeptides conjugated with IL-7<br>organism = synthetic construct | |
| SEQUENCE: 29<br>GGGGM | | 5 |
| SEQ ID NO: 30<br>FEATURE<br>source | moltype = AA   length = 5<br>Location/Qualifiers<br>1..5<br>mol_type = protein<br>note = oligopeptides conjugated with IL-7<br>organism = synthetic construct | |
| SEQUENCE: 30<br>MGMMM | | 5 |
| SEQ ID NO: 31<br>FEATURE<br>source | moltype = AA   length = 5<br>Location/Qualifiers<br>1..5<br>mol_type = protein<br>note = oligopeptides conjugated with IL-7<br>organism = synthetic construct | |
| SEQUENCE: 31<br>MGGMM | | 5 |
| SEQ ID NO: 32<br>FEATURE<br>source | moltype = AA   length = 5<br>Location/Qualifiers<br>1..5<br>mol_type = protein<br>note = oligopeptides conjugated with IL-7<br>organism = synthetic construct | |
| SEQUENCE: 32<br>MGGGM | | 5 |
| SEQ ID NO: 33<br>FEATURE<br>source | moltype = AA   length = 5<br>Location/Qualifiers<br>1..5<br>mol_type = protein<br>note = oligopeptides conjugated with IL-7<br>organism = synthetic construct | |
| SEQUENCE: 33<br>MGGGG | | 5 |
| SEQ ID NO: 34<br>FEATURE<br>source | moltype = AA   length = 5<br>Location/Qualifiers<br>1..5<br>mol_type = protein<br>note = oligopeptides conjugated with IL-7<br>organism = synthetic construct | |
| SEQUENCE: 34<br>MMGMM | | 5 |
| SEQ ID NO: 35<br>FEATURE<br>source | moltype = AA   length = 5<br>Location/Qualifiers<br>1..5<br>mol_type = protein<br>note = oligopeptides conjugated with IL-7<br>organism = synthetic construct | |
| SEQUENCE: 35<br>MMGGM | | 5 |
| SEQ ID NO: 36<br>FEATURE<br>source | moltype = AA   length = 5<br>Location/Qualifiers<br>1..5<br>mol_type = protein<br>note = oligopeptides conjugated with IL-7<br>organism = synthetic construct | |
| SEQUENCE: 36<br>MMGGG | | 5 |
| SEQ ID NO: 37<br>FEATURE<br>source | moltype = AA   length = 5<br>Location/Qualifiers<br>1..5<br>mol_type = protein<br>note = oligopeptides conjugated with IL-7<br>organism = synthetic construct | |
| SEQUENCE: 37 | | |

MMMGM                                                                          5

SEQ ID NO: 38          moltype = AA  length = 5
FEATURE                Location/Qualifiers
source                 1..5
                       mol_type = protein
                       note = oligopeptides conjugated with IL-7
                       organism = synthetic construct
SEQUENCE: 38
MMMGG                                                                          5

SEQ ID NO: 39          moltype = AA  length = 5
FEATURE                Location/Qualifiers
source                 1..5
                       mol_type = protein
                       note = oligopeptides conjugated with IL-7
                       organism = synthetic construct
SEQUENCE: 39
MMMMG                                                                          5

SEQ ID NO: 40          moltype = AA  length = 5
FEATURE                Location/Qualifiers
source                 1..5
                       mol_type = protein
                       note = oligopeptides conjugated with IL-7
                       organism = synthetic construct
SEQUENCE: 40
MGGGM                                                                          5

SEQ ID NO: 41          moltype = AA  length = 5
FEATURE                Location/Qualifiers
source                 1..5
                       mol_type = protein
                       note = oligopeptides conjugated with IL-7
                       organism = synthetic construct
SEQUENCE: 41
MGMGM                                                                          5

SEQ ID NO: 42          moltype = AA  length = 5
FEATURE                Location/Qualifiers
source                 1..5
                       mol_type = protein
                       note = oligopeptides conjugated with IL-7
                       organism = synthetic construct
SEQUENCE: 42
GMGMG                                                                          5

SEQ ID NO: 43          moltype = AA  length = 5
FEATURE                Location/Qualifiers
source                 1..5
                       mol_type = protein
                       note = oligopeptides conjugated with IL-7
                       organism = synthetic construct
SEQUENCE: 43
GMMMG                                                                          5

SEQ ID NO: 44          moltype = AA  length = 5
FEATURE                Location/Qualifiers
source                 1..5
                       mol_type = protein
                       note = oligopeptides conjugated with IL-7
                       organism = synthetic construct
SEQUENCE: 44
GGMGM                                                                          5

SEQ ID NO: 45          moltype = AA  length = 5
FEATURE                Location/Qualifiers
source                 1..5
                       mol_type = protein
                       note = oligopeptides conjugated with IL-7
                       organism = synthetic construct
SEQUENCE: 45
GGMMG                                                                          5

SEQ ID NO: 46          moltype = AA  length = 5
FEATURE                Location/Qualifiers
source                 1..5
                       mol_type = protein
                       note = oligopeptides conjugated with IL-7

```
                        organism = synthetic construct
SEQUENCE: 46
MGGMG                                                                       5

SEQ ID NO: 47           moltype = AA  length = 5
FEATURE                 Location/Qualifiers
source                  1..5
                        mol_type = protein
                        note = oligopeptides conjugated with IL-7
                        organism = synthetic construct
SEQUENCE: 47
MGMGG                                                                       5

SEQ ID NO: 48           moltype = AA  length = 5
FEATURE                 Location/Qualifiers
source                  1..5
                        mol_type = protein
                        note = oligopeptides conjugated with IL-7
                        organism = synthetic construct
SEQUENCE: 48
GMMGM                                                                       5

SEQ ID NO: 49           moltype = AA  length = 5
FEATURE                 Location/Qualifiers
source                  1..5
                        mol_type = protein
                        note = oligopeptides conjugated with IL-7
                        organism = synthetic construct
SEQUENCE: 49
MGMMG                                                                       5

SEQ ID NO: 50           moltype = AA  length = 5
FEATURE                 Location/Qualifiers
source                  1..5
                        mol_type = protein
                        note = oligopeptides conjugated with IL-7
                        organism = synthetic construct
SEQUENCE: 50
GMGGM                                                                       5

SEQ ID NO: 51           moltype = AA  length = 5
FEATURE                 Location/Qualifiers
source                  1..5
                        mol_type = protein
                        note = oligopeptides conjugated with IL-7
                        organism = synthetic construct
SEQUENCE: 51
MMGMG                                                                       5

SEQ ID NO: 52           moltype = AA  length = 5
FEATURE                 Location/Qualifiers
source                  1..5
                        mol_type = protein
                        note = oligopeptides conjugated with IL-7
                        organism = synthetic construct
SEQUENCE: 52
GMMGG                                                                       5

SEQ ID NO: 53           moltype = AA  length = 5
FEATURE                 Location/Qualifiers
source                  1..5
                        mol_type = protein
                        note = oligopeptides conjugated with IL-7
                        organism = synthetic construct
SEQUENCE: 53
GMGGG                                                                       5

SEQ ID NO: 54           moltype = AA  length = 5
FEATURE                 Location/Qualifiers
source                  1..5
                        mol_type = protein
                        note = oligopeptides conjugated with IL-7
                        organism = synthetic construct
SEQUENCE: 54
GGMGG                                                                       5

SEQ ID NO: 55           moltype = AA  length = 5
FEATURE                 Location/Qualifiers
source                  1..5
```

-continued

```
                    mol_type = protein
                    note = oligopeptides conjugated with IL-7
                    organism = synthetic construct
SEQUENCE: 55
GGGMG                                                                       5

SEQ ID NO: 56       moltype = AA  length = 5
FEATURE             Location/Qualifiers
source              1..5
                    mol_type = protein
                    note = oligopeptides conjugated with IL-7
                    organism = synthetic construct
SEQUENCE: 56
GGGGG                                                                       5
```